(12) United States Patent
Kunita

(10) Patent No.: US 6,451,497 B1
(45) Date of Patent: Sep. 17, 2002

(54) POSITIVE PHOTOSENSITIVE COMPOSITION

(75) Inventor: Kazuto Kunita, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/572,568

(22) Filed: May 16, 2000

(30) Foreign Application Priority Data

May 17, 1999 (JP) ............................................. 11-135341
May 17, 1999 (JP) ............................................. 11-135493

(51) Int. Cl.$^7$ ............................................. G03F 7/023
(52) U.S. Cl. ........................ 430/191; 430/192; 430/193; 534/558
(58) Field of Search ............................... 430/191, 192, 430/193; 534/558, 560

(56) References Cited

U.S. PATENT DOCUMENTS

2,759,817 A 8/1956 Schmidt et al. .................. 95/7
5,212,042 A 5/1993 Shinozaki et al. .......... 430/189

FOREIGN PATENT DOCUMENTS

EP 0833204 A1 4/1998

OTHER PUBLICATIONS

Chemical Abstracts, vol. 70, No. 23, Jun. 9, 1969, Columbus, Ohio, US; Abstract No. 106178z, Takamura et al; p. 303; col. 2; XP002146679.
Cecchi et al, "Synthesis and Reactivity of 1–Methyl–3–phenyl–4–diazo–5–benzoylamido–pyrazole. A Potential Antitumor Agent", Journal of Heterocyclic Chemistry, vol. 21, 1984, pp. 957–959, XP002146668.
Regitz et al; Liebigs Annalen Der Chemie, 1973, pp. 1505–1529, XP002146669, Weinheim DE.
Vicentini C.B. et al; "4–Diazo–5–alkylsulphonamidopyrazoles: Synthesis and evaluation of biological activity", Farmaco., vol. 46, No. 11, 1991, pp. 1351–1363.
Daidone G. et al; "Antimicrobial and antineoplastic activities of new 4–diazopyrazole derivatives", Eur. J. Med. Chem, vol. 33, 1998, pp. 375–382, XP002146671.
Harmon R.E. et al; "N,N–Dialkylamino–,2,3–triazole–α–diazoamidine Tautomers from Substituted Benzenesulfonyl Azides and Ynamines", J. of Organic Chem., vol. 35, No. 10, 1970, pp. 3444–3448, XP002146672.

Harmon R.E. et al; "The Reaction of Arylsulfonyl Azides with N–Methylindole", J. of Organic Chem., vol. 38, No. 1, 1973, pp. 11–16, XP002146673.
Regitz M. et al; "Ueber das 5–Alkoxy–1,2,3–triazol/α–Diazo–carbonimidsaeure–alkylester–Gleichgewicht", vol. 105, 1972, pp. 2975–2984, XP002146674.
Regitz M. et al; "Diazogruppen–Uebertragung auf (Phosphorylaetinyl)amine", vol. 107, 1974, pp. 2513–2536, XP002146675.
Bailey A.S. et al; "The Reactions of Arenesulphonyl Azides with Indole and with 1–Methyl–indole", J. of the Chem. Soc., 1972, pp. 2411–2415, XP002156676.
Daidone G. et al; "Synthesis and Antineoplastic Activity of New 4–Diazopyrazole Derivatives", Farmaco., vol. 52, 1997, pp. 557–559, XP002146677.
Regitz M. et al: Synthesis., 1972, pp. 571–573, XP002146678 Georg Thieme Verlag, Stuttgart., DE ISSN: 0039–7881.
Harmon R.E. et al; "N.m.r. spectral studies on N,N–dialkylamino–1,2,3–triazole–α–diazoamidine equilibrium", Chem. and Industry. Chemistry and Industry Review., Aug. 1, 1970, pp. 1021–1022, XP000911931.
Ondrus T. A. et al; "Some reactions of 1,2–dihydropyridines with organic azides. Synthesis of diazabicylo . . .", Canadian J. of Chemistry, vol. 57, No. 18, 1979, pp. 2342–2349, XP000938820.
Diadone G. et al; "Facile Synthesis of 5–Benzamido–4–Diazopyrazole Derivatives, A Class of Biologically Active Agents", Syn. Comm., vol. 25, No. 10, 1995, pp. 1441–1449, XP000911935.

*Primary Examiner*—John S. Chu
(74) *Attorney, Agent, or Firm*—Burns, Doane, Swecker & Mathis, LLP

(57) ABSTRACT

The present invention relates to a positive photosensitive composition, and in particular to a material for plate printing for heat mode printing. The positive photosensitive composition of the present invention comprises at least a diazo compound represented by the following General Formula 1, and a water-insoluble but alkaline water-soluble polymer:

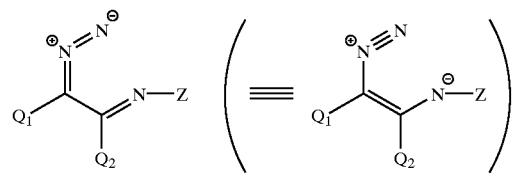

(where Z represents an organic group in which the pKa of dissociating H in Ph—NH—Z is 14 or less; and $Q^1$ and $Q^2$ represent organic groups, where $Q^1$ and $Q^2$ may be bonded to form an aliphatic ring or aromatic ring).

23 Claims, No Drawings

POSITIVE PHOTOSENSITIVE COMPOSITION

BACKGROUND OF THE INVENTION

1. Field of the Invention

The present invention generally relates to a positive photosensitive composition having photosensitivity in the infrared wavelength range, and more particularly to a positive photosensitive composition that is suitable for lithographic photoresists or printing material for what is referred to as direct plateable positive lithography, which allows plates to be directly produced using an infrared laser based on digital signals from a computer or the like.

2. Description of the Related Art

Laser development has been quite remarkable recently. Solid-state lasers and semiconductor lasers in particular, which emit infrared rays having a wavelength ranging from 760 to 1200 nm (hereinafter referred to as "infrared lasers"), are now readily available in the form of small-scale models with high output. Such infrared lasers are extremely useful as printing light sources during the direct production of printing plates based on digital data from computers and the like. There has thus been increasing demand recently for materials that can be used as image recording materials, particularly heat mode laser image recording materials, with high sensitivity for such infrared printing light sources.

Typical examples of positive image recording materials for heat mode lasers include printing materials featuring the use of quinone diazides or diazonium salts such as those disclosed in Japanese Patent Application Laid-Open (JP-A) No.7-285275. Such positive image recording materials utilize dissolution inhibiting effects brought about by the interaction between quinone diazides or diazonium salts, infrared absorbents, and alkaline water-soluble polymers. The quinone diazides or diazonium salts are decomposed upon exposure to laser light, breaking down this interaction, and the parts that are exposed to light are dissolved in alkaline water during development to form positive images. The desired dissolution of the quinone diazides or diazonium salts referred to here means dissolution whereby acid is produced upon reaction with moisture in the system. The acid that is produced facilitates development.

Heat mode exposure systems do not have as much system moisture as UV exposure systems, however, and are thus incapable of producing enough acid from quinone diazides or diazonium salts. One problem, for example, is that the interaction between the infrared absorbent and alkaline water-soluble polymer is restored when allowed to stand for several hours after light exposure, resulting in lower sensitivity and incapacitated development.

As noted above, it has not been possible in the past to obtain a positive photosensitive composition with high sensitivity to heat mode lasers, good development latitude, and good storage stability.

SUMMARY OF THE INVENTION

An object of the present invention is to provide a positive photosensitive composition with high sensitivity to heat mode lasers, good development latitude, and good storage stability.

As a result of extensive research, the inventors perfected the present invention upon finding that the aforementioned drawbacks can be resolved by the following means.

Specifically, the positive photosensitive composition of the present invention comprises at least a diazo compound represented by the following General Formula 1, and a water-insoluble but alkaline water-soluble polymer:

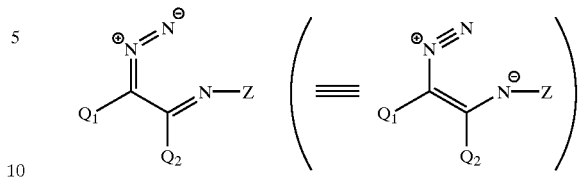

(where Z represents an organic group in which the pKa of dissociating H in Ph—NH—Z is 14 or less; and $Q^1$ and $Q^2$ represent organic groups, where $Q^1$ and $Q^2$ may be bonded to form an aliphatic ring or aromatic ring).

The organic group z referred to here is preferably —$SO_2R^1$ or —$COR^2$ (where $R^1$ represents a hydrocarbon group, and $R^2$ represents a hydrocarbon group with an electron-attracting substituent), and the hydrocarbon group $R^2$ preferably has any electron-attractive substituent selected from the group consisting of halogen atoms, substituted sulfonyl groups, nitro groups, cyano groups, alkoxy groups, and hydroxy groups.

The positive photosensitive composition of the present invention also preferably further comprises an infrared absorbent.

It is assumed that the development properties during exposure are not improved very much in conventional positive image recording materials for heat mode lasers because the quinone diazides or diazonium salts contained in the material produce intermediates that are highly reactive during exposure-induced decomposition, and that the intermediates become insoluble upon reaction with the alkaline water-soluble polymer serving as the binder.

For example, the naphthoquinone diazide used in positive image recording materials with UV exposure produce highly reactive ketenes when decomposed upon exposure. In UV light systems, the ketenes react with moisture in the material and are inactivated in the form of carboxylic acids, but it is assumed that the elevated heat in heat mode systems results in less moisture in the material and prevents the ketenes from reacting with water molecules, and that these ketenes react with the alkaline water-soluble polymer, rendering the alkaline water-soluble polymer insoluble.

A feature of the positive photosensitive composition of the present invention is the use of a diazo compound represented by the aforementioned General Formula 1 as an acid-producing agent. Because of its inherent structure, the diazo compound is believed to selectively react with water molecules to facilitate development during exposure, without producing ketenes that are highly reactive with alkaline water-soluble polymers when decomposed upon exposure.

DESCRIPTION OF THE PREFERRED EMBODIMENTS

The positive photosensitive composition of the present invention is described in detail below.

(A) Diazo Compounds Represented by General Formula 1

The diazo compounds of the present invention are characterized by being represented by the following General Formula 1.

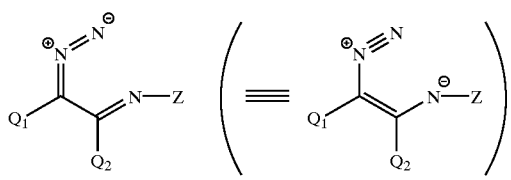

(1)

In General Formula 1, Z represents an organic group selected so that the pKa of the dissociating hydrogen in compound Ph—NH—Z, where the amino group of Ph—$NH_2$ is substituted by Z, is 14 or less. The organic group Z is not particularly limited, provided that it meets these conditions, although —$SO_2R^1$ and —$COR^2$ (where $R^1$ represents a hydrocarbon group, and $R^2$ represents a hydrocarbon group with an electron-attracting substituent) are particularly preferred.

The hydrocarbon group $R^1$ of the organic group —$SO_2R^1$ may have a substituent, and may include an unsaturated bond. Examples of such hydrocarbon groups include alkyl groups, substituted alkyl groups, aryl groups, substituted aryl groups, alkenyl groups, substituted alkenyl groups, alkinyl groups, and substituted alkinyl groups.

Examples of alkyl groups include $C_1$ to $C_{20}$ linear, branched, or cyclic alkyl groups, specific examples of which include methyl, ethyl, propyl, butyl, pentyl, hexyl, heptyl, octyl, nonyl, decyl, undecyl, dodecyl, tridecyl, hexadecyl, octadecyl, eicosyl, isopropyl, isobutyl, sec-butyl, tert-butyl, isopentyl, neopentyl, 1-methylbutyl, isohexyl, 2-ethylhexyl, 2-methylhexyl, cyclohexyl, cyclopentyl, and 2-norbornyl groups. Of these, $C_1$ to $C_{12}$ linear alkyls, $C_3$ to $C_{12}$ branched alkyls, and $C_5$ to $C_{10}$ cyclic alkyls are preferred.

Substituted alkyl groups are composed by a bond between the substituent and alkylene group. Monovalent nonmetallic atom groups except for hydrogen are used as substituents. Preferred examples include halogen atoms (—F, —Br, —Cl, —I), hydroxy groups, alkoxy groups, aryloxy groups, mercapto groups, alkylthio groups, arylthio groups, alkyldithio groups, aryldithio groups, amino groups, N-alkylamino groups, N,N-dialkylamino groups, N-arylamino groups, N,N-diarylamino groups, N-alkyl-N-arylamino groups, acyloxy groups, carbamoyloxy groups, N-alkylcarbamoyloxy groups, N-arylcarbamoyloxy groups, N,N-dialkylcarbamoyloxy groups, N,N-diarylcarbamoyloxy groups, N-alkyl-N-arylcarbamoyloxy groups, alkylsulfoxy groups, arylsulfoxy groups, acylthio groups, acylamino groups, N-alkylacylamino groups, N-arylacylamino groups, ureido groups, N'-alkylureido groups, N',N'-dialkylureido groups, N'-arylureido groups, N',N'-diarylureido groups, N'-alkyl-N'-arylureido groups, N-alkylureido groups, N-arylureido groups, N'-alkyl-N-alkylureido groups, N'-alkyl-N-arylureido groups, N',N'-dialkyl-N-alkylureido groups, N',N'-dialkyl-N-arylureido groups, N'-aryl-N-alkylureido groups, N'-aryl-N-arylureido groups, N',N'-diaryl-N-alkylureido groups, N',N'-diaryl-N-arylureido groups, N'-alkyl-N'-aryl-N-alkylureido groups, N'-alkyl-N'-aryl-N-arylureido groups, alkoxycarbonylamino groups, aryloxycarbonylamino groups, N-alkyl-N-alkoxycarbonylamino groups, N-alkyl-N-aryloxycarbonylamino groups, N-aryl-N-alkoxycarbonylamino groups, N-aryl-N-aryloxycarbonylamino groups, formyl groups, acyl groups, carboxy groups and their conjugate base groups (hereinafter referred to as carboxylates), alkoxycarbonyl groups, aryloxycarbonyl groups, carbamoyl groups, N-alkylcarbamoyl groups, N,N-dialkylcarbamoyl groups, N-arylcarbamoyl groups, N,N-diarylcarbamoyl groups, N-alkyl-N-arylcarbamoyl groups, alkylsulfinyl groups, arylsulfinyl groups alkylsulfonyl groups, arylsulfonyl groups, sulfo groups (—$SO_3H$) and their conjugate base groups (hereinafter referred to as sulfonate groups), alkoxysulfonyl groups, aryloxysulfonyl groups, sulfinamoyl groups, N-alkylsulfinamoyl groups, N,N-dialkylsulfamoyl groups, N-arylsulfamoyl groups, N,N-diarylsulfinamoyl groups, N-alkyl-N-arylsulfinamoyl groups, sulfamoyl groups, Nalkylsulfamoyl groups, N,N-dialkylsulfainoyl groups, N-arylsulfamoyl groups, N,N-diarylsulfamoyl groups, N-alkyl-N-arylsulfamoyl groups, N-acylsulfamoyl groups and their conjugate base groups, N-alkylsulfonylsulfamoyl groups (—$SO_2NHSO_2$ (aryl)) and their conjugate base groups, N-ar ylsulfonylsulfamoyl groups (—$SO_2NHSO_2$ (allyl)) and their conjugate base groups, N-alkylsulfonylcarbamoyl groups (—$CONHSO_2$ (alkyl)) and their conjugate base groups, N-arylsulfonylcarbamoyl groups (—$CONHSO_2$ (aryl)) and their conjugate base groups, alkoxysilyl groups (—$Si(Oalkyl)_3$), aryloxysilyl groups (—$Si(Oaryl)_3$), hydroxysilyl groups (—$Si(OH)_3$) and their conjugate base groups, phosphono groups (—$PO_3H_2$) and their conjugate base groups (hereinafter referred to as phosphonato groups), dialkylphosphono groups (—$PO_3$ (alkyl)$_2$), diarylphosphono groups (—$PO_3$ (aryl)$_2$), alkylallylphosphono groups (—$PO_3$ (alkyl) (aryl), monoalkylphosphono groups (—$PO_3H$ (alkyl)) and their conjugate base groups (hereinafter referred to as alkylphosphonato groups), monoallylphosphono groups (—$PO_3H$ (aryl)) and their conjugate base groups (hereinafter referred to as allylphosphonato groups), phosphonoxy groups (—$OPO_3H_2$) and their conjugate base groups (hereinafter referred to as phosphonatoxy groups), dialkylphosphonoxy groups (—$OPO_3(alkyl)_2$), diallylphosphonoxy groups (—$OPO_3(aryl)_2$), alkylallylphosphonoxy groups (—$OPO_3$ (alkyl) (aryl), monoalkylphosphonoxy groups (—$OPO_3H$ (alkyl) and their conjugate base groups (hereinafter referred to as alkylphosphonatoxy groups), monoarylphosphonoxy groups (—$OPO_3H(aryl)$) and their conjugate base groups (hereinafter referred to as allylphosphonatoxy groups), cyano groups, nitro groups, aryl groups, alkenyl groups, and alkynyl groups.

Specific examples of alkyl groups in these substituents include the aforementioned alkyl groups. Specific examples of aryl groups include phenyl, biphenyl, naphthyl, tolyl, xylyl, mesityl, cumenyl, fluorophenyl, chlorophenyl, bromophenyl, chloromethylphenyl, hydroxyphenyl, methoxyphenyl, ethoxyphenyl, phenoxyphenyl, acetoxyphenyl, benzoyloxyphenyl, methylthiophenyl, phenylthiophenyl, methylaminophenyl, dimethylaminophenyl, acetylaminophenyl, carboxyphenyl, methoxycarbonylphenyl, ethoxycarbonylphenyl, phenoxycarbonylphenyl, N-phenylcarbamoylphenyl, phenyl, nitrophenyl, cyanophenyl, sulfophenyl, sulfonatophenyl, phosphonophenyl, and phosphonatophenyl groups. Examples of alkenyl groups include vinyl, 1-propenyl, 1-butenyl, cinnamyl, and 2-chloro-1-ethenyl groups. Examples of alkinyl groups include ethinyl, 1-propinyl, 1-butinyl, trimethylsilylethinyl, and phenylethinyl groups.

Of the aforementioned substituents, electron attractive substituents such as halogen atoms, nitro groups, and substituted carbonyl groups are preferred.

Examples of aryl groups include those forming condensed rings with 1 to 3 benzene rings, and those forming condensed rings with benzene rings and 5-membered unsaturated rings. Specific examples include phenyl, naphthyl, anthryl, phenanthryl, indenyl, acenaphthenyl, and fluorenyl groups. Of these, phenyl and naphthyl are preferred.

Substituted aryl groups used in the invention have the substituent bonded to the aryl group, and have a monovalent nonmetallic atomic group except for hydrogen as the substituent on the ring-forming carbon atom of the aforementioned aryl group. Examples of desirable substituents include the aforementioned alkyl groups, substituted alkyl groups, and those given earlier as examples of substituents for substituted alkyl groups. Specific examples of desirable substituted aryl groups include biphenyl, tolyl, xylyl, mesityl, cumenyl, chlorophenyl, bromophenyl, fluorophenyl, chloromethylphenyl, trifluoromethylphenyl, hydroxyphenyl, methoxyphenyl, methoxyethoxyphenyl, allyloxyphenyl, phenoxyphenyl, methylthiophenyl, tolylthiophenyl, phenylthiophenyl, ethylaminophenyl, diethylaminophenyl, morpholinophenyl, acetyloxyphenyl, benzoyloxyphenyl, N-cyclohexylcarbamoyloxyphenyl, N-phenylcarbamoyloxyphenyl, acetylaminophenyl, N-methylbenzoylaminophenyl, carboxyphenyl, methoxycarbonylphenyl, allyloxycarbonylphenyl, chlorophenoxycarbonylphenyl, carbamoylphenyl, N-methylcarbamoylphenyl, N,N-dipropylcarbamoylphenyl, N-(methoxyphenyl)carbamoylphenyl, N-methyl-N-(sulfophenyl)carbamoylphenyl, sulfophenyl, sulfonatophenyl, sulfamoylphenyl, N-ethylsulfamoylphenyl, N,N-dipropylsulfamoylphenyl, N-tolylsulfamoylphenyl, N-methyl-N-(phosphonophenyl)sulfamoylphenyl, phosphonophenyl, phosphonatophenyl, diethylphosphonophenyl, diphenylphosphonophenyl, methylphosphonophenyl, methylphosphonatophenyl, tolylphosphonophenyl, tolylphosphonatophenyl, allyl, 1-propenylmethyl, 2-butenyl, 2-methylallylphenyl, 2-methylpropenylphenyl, 2-propinylphenyl, 2-butinylphenyl, and 3-butinylphenyl.

Examples of alkenyl groups include vinyl, 1-propenyl, 1-butenyl, cinnamyl, and 2-chloro-1-ethenyl groups. In substituted alkenyl groups, the substituent replaces the hydrogen atom of the alkenyl groups. Examples of such substituents include the substituents in the aforementioned substituted alkyl groups.

The following are examples of preferred substituted alkenyl groups.

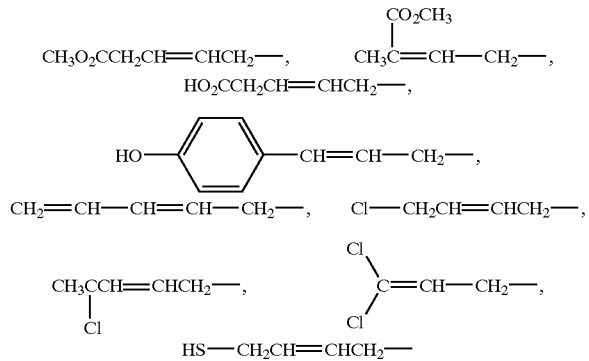

Examples of alkinyl groups include ethinyl, 1-propinyl, 1-butinyl, trimethylsilylethinyl, and phenylethinyl groups. In substituted alkinyl groups, the substituent is bonded instead of the hydrogen atom of the alkinyl groups. Examples of such substituents include the substituents in the aforementioned substituted alkyl groups.

The hydrocarbon $R^2$ having an electron attracting substituent group in the organic group —$COR^2$ may have a substituent, and may include an unsaturated bond. Examples of hydrocarbon groups include the same alkyl groups, allyl groups, alkenyl groups, and alkinyl groups as for the hydrocarbon group $R^1$. Those having a halogen atom, substituted sulfonyl group, nitro group, cyano group, alkoxy group, or hydroxy group as the electron attracting substituent are preferred.

$Q^1$ and $Q^2$ in General Formula represent organic groups. $Q^1$ and $Q^2$ may be the same as or different from each other. $Q^1$ and $Q^2$ may also be bonded together to form a ring.

Examples of organic groups $Q^1$ and $Q^2$ include hydrocarbon groups, heterocyclic groups, substituted oxy groups, substituted thio groups, substituted amino groups, substituted carbonyl groups, substituted sulfinyl groups, substituted sulfonyl groups, substituted phosphono groups, substituted phosphonato groups, substituted phosphoryl groups, and cyano groups.

The hydrocarbon groups represented by $Q^1$ and $Q^2$ may have substituents and may include unsaturated bonds. Examples of hydrocarbon groups represented by $Q^1$ and $Q^2$ include the same alkyl groups, substituted alkyl groups, allyl groups, substituted allyl groups, alkenyl groups, substituted alkenyl groups, alkinyl groups, and substituted alkinyl groups as for the hydrocarbon group $R^1$.

Heterocyclic groups are monovalent groups with one hydrogen on the hetero ring removed, and monovalent groups (substituted heterocyclic groups) with another hydrogen removed from the above monovalent group, having substituents from among the aforementioned substituted alkyl groups bonded thereto.

The following heterocyclic groups are preferred as the hetero ring represented by $Q^1$ and $Q^2$.

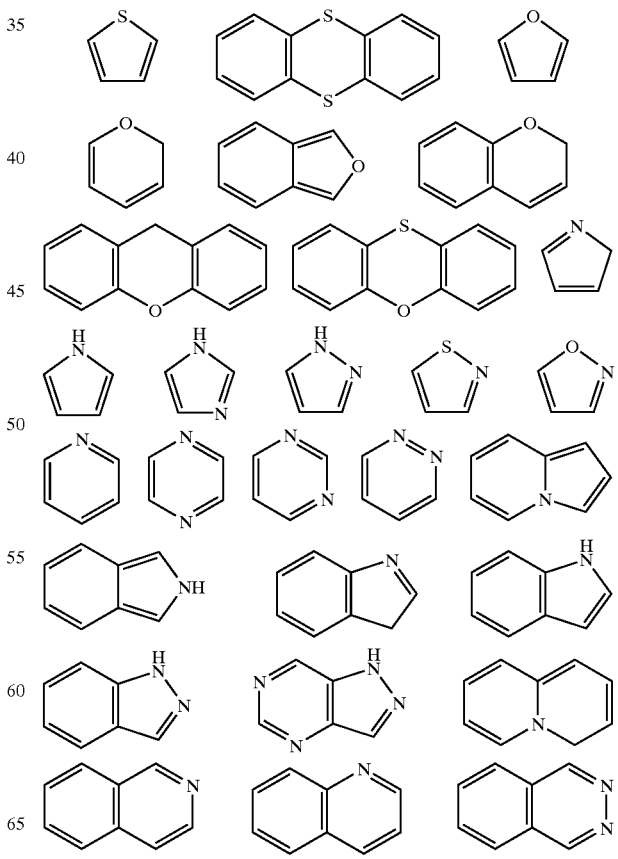

-continued

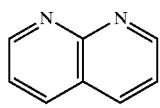 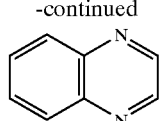 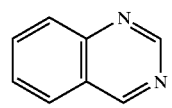

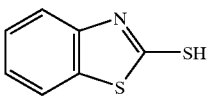 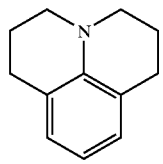 

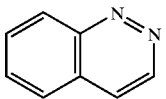 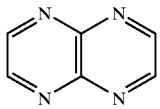

 

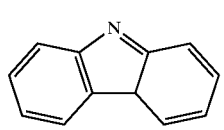 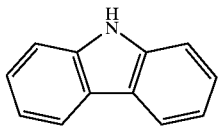

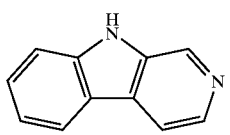 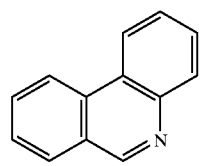

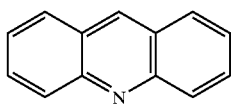 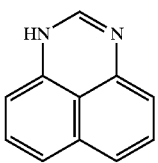

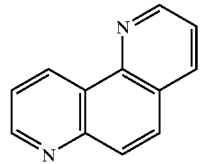 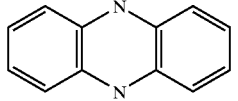

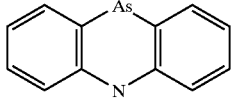 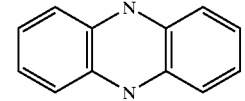

 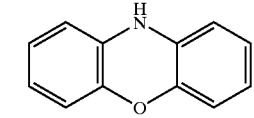 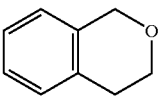

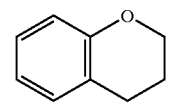 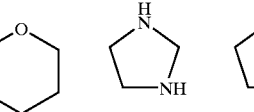 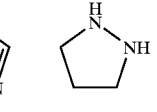

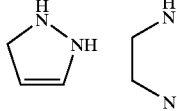 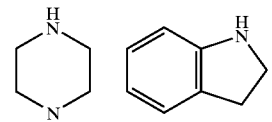 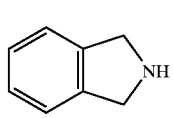

 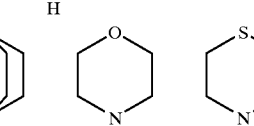 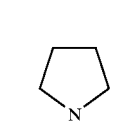

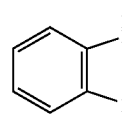 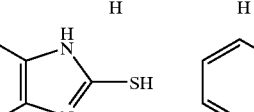 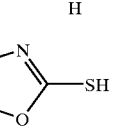

Examples of substituted oxy groups ($R^5O—$) represented by $Q^1$ and $Q^2$ which can be used include those in which $R^1$ is a monovalent nonmetallic atomic group except for hydrogen. Examples of desirable substituted oxy groups include alkoxy, aryloxy, acyloxy, carbamoyloxy, N-alkylcarbamoyloxy, N-arylcarbamoyloxy, N,N-dialkylcarbamoyloxy, N,N-diarylcarbamoyloxy, N-alkyl-N-arylcarbamoyloxy, alkylsulfoxy, arylsulfoxy, phosphonoxy, and phosphonatoxy groups. Examples of alkyl and allyl groups for these include the aforementioned alkyl, substituted alkyl, aryl, and substituted aryl groups. Examples of acyl groups ($R^6CO—$) for acyloxy groups include those in which $R^6$ is an aforementioned alkyl, substituted alkyl, aryl, or substituted aryl group. Alkoxy groups, aryloxy groups, acyloxy groups, and arylsulfoxy groups are preferred among such substituents. Specific examples of preferred substituted oxy groups include methoxy, ethoxy, propyloxy, isopropyloxy, butyloxy, pentyloxy, hexyloxy, dodecyloxy, benzyloxy, allyloxy, phenethyloxy, carboxyethyloxy, methoxycarbonylethyloxy, ethoxycarbonylethyloxy, methoxyethoxy, phenoxyethoxy, methoxyethoxyethoxy, ethoxyethoxyethoxy, morpholinoethoxy, morpholinopropyloxy, allyloxyethoxyethoxy, phenoxy, tolyloxy, xylyloxy, mesityloxy, cumenyloxy, methoxyphenyloxy, ethoxyphenyloxy, chlorophenyloxy, bromophenyloxy, acetyloxy, benzoyloxy, naphthyloxy, phenylsulfonyloxy, phosphonoxy, and phosphonatoxy groups.

Examples of substituted thio groups ($R^7S—$) represented by $Q^1$ and $Q^2$ include those in which $R^7$ is a monovalent nonmetallic atomic group except for hydrogen. Examples of desirable substituted thio groups include alkythio groups, arylthio groups, alkyldithio groups, aryldithio groups, and acylthio groups. Examples of alkyl and aryl groups for these include the aforementioned alkyl, substituted alkyl, aryl, and substituted aryl groups. $R^6$ of the acyl group ($R^6CO—$) in acylthio groups are the same as above. Alkylthio and arylthio groups are preferred among these. Specific examples of desirable substituted thio groups include methylthio, ethylthio, phenylthio, ethoxyethylthio, carboxyethylthio, and methoxycarbonylthio groups.

Examples of substituted amino groups ($R^8NH—$, ($R^9$)($R^{10}$)N—) represented by $Q^1$ and $Q^2$ which can be used include those in which $R^8$, $R^9$, and $R^{10}$ are monovalent nonmetallic atomic groups except for hydrogen. Preferred examples of substituted amino groups include N-alkylamino group, N,N-dialkylamino groups, N-arylamino groups, N,N-diarylamino groups, N-alkyl-N-arylamino groups, acylamino groups, N-alkylacylamino groups, N-arylacylamino groups, ureido groups, N'-alkylureido groups, N',N'-dialkylureido groups, N'-arylureido groups, N',N'-diarylureido groups, N'-alkyl-N'-arylureido groups, N-alkylureido groups, N-arylureido groups, N'-alkyl-N-alkylureido groups, N'-alkyl-N-arylureido groups, N',N'- dialkyl-N-alkylureido groups, N',N'-dialkyl-N-arylureido groups, N'-aryl-N-alkylureido groups, N'-aryl-N-arylureido groups, N',N'-diaryl-N-alkylureido groups, N',N'-diaryl-N-arylureido groups, N'-alkyl-N'-aryl-N-alkylureido groups, N'-alkyl-N'-aryl-N-arylureido groups, alkoxycarbonylamino groups, aryloxycarbonylamino groups, N-alkyl-N-alkoxycarbonylamino groups, N-alkyl-N-aryloxycarbonylamino groups, N-aryl-N-alkoxycarbonylamino groups, and N-aryl-N-aryloxycarbonylamino groups. The aforementioned alkyl, substituted alkyl, aryl, and substituted aryl groups can be used as alkyl and aryl groups here. $R^6$ of the acyl group ($R^6CO$—) in acylamino groups, N-alkylacylamino groups, and N-arylacylamino groups is the same as above. N-alkylamino groups, N,N-dialkylamino groups, N-arylamino groups, and acylamino groups are preferred among these. Specific examples of desirable substituted amino groups include methylamino, ethylamino, diethylamino, morpholino, piperidino, pyrrolidino, phenylamino, benzoylamino, and acetylamino groups.

Examples of substituted carbonyl groups ($R^{11}$—CO—) represented by $Q^1$ and $Q^2$ include those in which $R^{11}$ is a monovalent nonmetallic atomic group. Desirable examples of substituted carbonyl groups include formyl, acyl, carboxy, alkoxycarbonyl, aryloxycarbonyl, carbamoyl, N-alkylcarbamoyl, N,N-dialkylcarbamoyl, N-arylcarbamoyl, N,N-diarylcarbamoyl, and N-alkyl-N-arylcarbamoyl groups. The aforementioned alkyl, substituted alkyl, aryl, and substituted aryl groups can be used as alkyl and aryl groups here. Examples of more desirable substituents among these include formyl, acyl, carboxy, alkoxycarbonyl, aryloxycarbonyl, carbamoyl, N-arylcarbamoyl, N,N-dialkylcarbamoyl, and N-arylcarbamoyl groups. Even more desirable examples include formyl, acyl, alkoxycarbonyl, and aryloxycarbonyl groups. Specific examples of desirable substituents include formyl, acetyl, benzoyl, carboxy, methoxycarbonyl, allyloxycarbonyl, N-methylcarbamoyl, N-phenylcarbamoyl, N,N-diethylcarbamoyl, and morpholinocarbonyl groups.

Examples of substituted sulfinyl groups ($R^{12}$—SO—) represented by $Q^1$ and $Q^2$ include those in which $R^{12}$ is a monovalent nonmetallic atomic group. Desirable examples include alkinylsufinyl, arylsulfinyl, sulfinamoyl, N-alkylsulfinamoyl, N,N-dialkylsulfinamoyl, N-arylsulfinamoyl, N,N-diarylsufinamoyl, and N-alkyl-N-arylsulfinamoyl groups. The aforementioned alkyl, substituted alkyl, aryl, and substituted aryl groups can be used as alkyl and aryl groups here. Examples that are preferred among these include alkylsulfinyl and arylsulfinyl groups. Specific examples of such substituted sulfinyl groups include hexylsulfinyl, benzylsulfinyl, and tolylsulfinyl groups.

Examples of substituted sulfonyl groups ($R^{13}$—$OS_2$—) represented by $Q^1$ and $Q^2$ include those in which $R^{13}$ is a monovalent nonmetallic atomic group. Preferred examples include alkylsulfonyl and arylsulfonyl groups. The aforementioned alkyl, substituted alkyl, aryl, and substituted aryl groups can be used as alkyl and aryl groups here. Specific examples of such substituted sulfonyl groups include butylsulfonyl and chlorophenylsulfonyl groups.

Substituted phosphono groups mean those in which one or two hydroxyl groups on the phosphono group have been substituted by another organic oxo group. Desirable examples of substituted phosphono groups represented by $Q^1$ and $Q^2$ include the aforementioned dialkylphosphono groups, diarylphosphono groups, alkylarylphosphono groups, monoalkylphosphono, and monoarylphosphono groups. Dialkylphosphono and diarylphosphono groups are preferred among these. Specific examples include diethylphosphono, dibutylphosphono, and diphenylphosphono groups.

Substituted phosphonato groups are conjugate base anion groups of the aforementioned phosphono groups in which one hydroxyl group has been substituted with an organic oxo group. Specific examples include the conjugate base groups of the aforementioned monoalkylphosphono (—$PO_3H$ (alkyl)) and monoarylphosphono (—$PO_3H$ (aryl)) groups. Ordinarily, they are preferably used with counter cations. Examples of such counter cations include those which are commonly known, such as various oniums (ammonium, sulfonium, phosphonium, iodonium, azinium, and the like) and metal ions (such as $Na^+$, $K+$, $Ca^{2+}$, and $Zn^{2+}$)

Examples of phosphoryl groups represented by $Q^1$ and $Q^2$ include diphenylphosphoryl.

Hydrocarbon groups, substituted carbonyl groups, and substituted phosphoryl groups are preferred as organic groups represented by $Q^1$ and $Q^2$ among the aforementioned substituents. Hydrocarbon groups preferably include hetero atoms.

The organic groups $Q^1$ and $Q^2$ preferably are bonded together to form aliphatic rings or aromatic rings. Aromatic rings such as benzene rings, naphthalene rings, or anthracene rings are preferably formed for the sake of more stable conjugation.

The rings may also have substituents. Examples of substituents include those given as examples of substituents for the aforementioned substituted alkyl groups. Some of the ring constituent carbons may also be substituted by hetero atoms (such as oxygen, sulfur, and nitrogen atoms). Some of the aliphatic rings may also form some of the aromatic rings.

The organic groups $Q^1$ and $Q^2$ may also be substituted by a residue of General Formula 1.

The following are specific examples of diazo compounds represented by General Formula 1.

TABLE 1

| Compound No. | Z |
|---|---|
| A-1 | —$SO_2$—C6H4—$CH_3$ |
| A-2 | —$SO_2$—C6F4—F (pentafluorophenyl) |
| A-3 | —$SO_2CH_3$ |
| A-4 | —$SO_2C_4H_9$ |
| A-5 | —$SO_2CF_3$ |
| A-6 | —$SO_2C_8F_{17}$ |

TABLE 1-continued

[Structure: naphthalene with =N-Z and =N₂ groups]

| Compound No. | Z |
|---|---|
| A-7 | —SO₂-(1-naphthyl) |
| A-8 | —SO₂-C₆H₄-NO₂ (para) |
| A-9 | —SO₂-C₆H₄-Cl (ortho) |
| A-10 | —COCF₃ |
| A-11 | —COCCl₃ |
| A-12 | —COCBr₃ |
| A-13 | —CO-C₆F₅ (pentafluorophenyl) |
| A-14 | —COCH₂CN |
| A-15 | —COCH₂OC₂H₅ |
| A-16 | —CO-C₆H₃(NO₂)₂ (2,4-dinitrophenyl) |
| A-17 | —CO-C₆H₄-SO₃CH₃ (para) |
| A-18 | —CO-C₆H₄-CN (ortho) |
| A-19 | —CO-(2-chlorocyclohexyl) |
| A-20 | —SO₂-cyclohexyl |
| A-21 | —SO₂-CH(CH₃)₂ |
| A-22 | —SO₂CH₂-(camphor group) |

TABLE 2

[Structure: naphthalene with =N₂ and =N-Z groups]

| Compound No. | Z |
|---|---|
| B-1 | —SO₂-C₆H₄-CH₃ (para) |
| B-2 | —SO₂-C₆F₅ (pentafluorophenyl) |
| B-3 | —SO₂CH₃ |
| B-4 | —SO₂C₄H₉ |
| B-5 | —SO₂CF₃ |
| B-6 | —SO₂C₈F₁₇ |
| B-7 | —SO₂-(1-naphthyl) |
| B-8 | —SO₂-C₆H₄-NO₂ (para) |
| B-9 | —SO₂-C₆H₄-Cl (ortho) |
| B-10 | —COCF₃ |
| B-11 | —COCCl₃ |
| B-12 | —COCBr₃ |

TABLE 2-continued
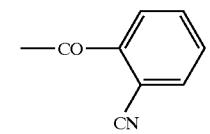
| Compound No. | Z |
|---|---|
| B-13 | 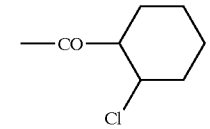 |
| B-14 | —COCH₂CN |
| B-15 | —COCH₂OC₂H₅ |
| B-16 | 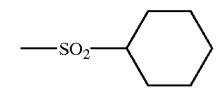 |
| B-17 | 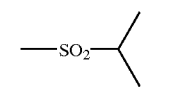 |
| B-18 | 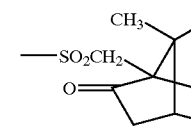 |
| B-19 | 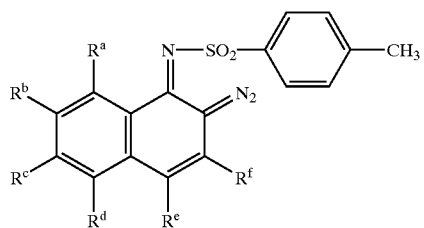 |
| B-20 | —SO₂— (cyclohexyl) |
| B-21 | —SO₂—CH(CH₃)₂ |
| B-22 |  |
TABLE 3
| Compound No. | Rᵃ | Rᵇ | Rᶜ | Rᵈ | Rᵉ | Rᶠ |
|---|---|---|---|---|---|---|
| C-1 | H | —SO₃—Ph | H | H | H | H |
| C-2 | H | H | —SO₃—C₆H₄—CH₃ | H | H | H |

TABLE 3-continued

[Structure: naphthalene core with substituents $R^a$ (position 8), $R^b$, $R^c$, $R^d$, $R^e$, $R^f$; at position 1: =N—SO$_2$—C$_6$H$_4$—CH$_3$ (p-tolyl); at position 2: =N$_2$]

| Compound No. | $R^a$ | $R^b$ | $R^c$ | $R^d$ | $R^e$ | $R^f$ |
|---|---|---|---|---|---|---|
| C-3 | H | H | H | —SO$_3$—C$_6$H$_4$—CH$_3$ (p-tolyl) | H | H |
| C-4 | H | H | H | —SO$_3$—(1-naphthyl) | H | H |
| C-5 | H | H | H | —SO$_3$—C$_6$H$_4$—OCH$_3$ (p-methoxyphenyl) | H | H |
| C-6 | H | H | H | —SO$_3$—cyclohexyl | H | H |
| C-7 | H | H | H | —SO$_3$C$_8$H$_{17}$(n) | H | H |

TABLE 4

[Structure: naphthalene core with substituents $R^a$, $R^b$, $R^c$, $R^d$, $R^e$, $R^f$; at position 1: =N—SO$_2$—C$_6$H$_4$—CH$_3$ (p-tolyl); at position 2: =N$_2$]

| Compound No. | $R^a$ | $R^b$ | $R^c$ | $R^d$ | $R^e$ | $R^f$ |
|---|---|---|---|---|---|---|
| C-8 | H | H | H | H | —SO$_3$—C$_6$H$_4$—CH$_3$ (p-tolyl) | H |
| C-9 | H | H | H | H | —SO$_3$—C$_6$H$_4$—C(CH$_3$)$_2$CH$_2$C(CH$_3$)$_3$ | H |
| C-10 | H | H | Cl | H | H | H |
| C-11 | H | H | H | H | —SC$_{12}$H$_{25}$(n) | H |
| C-12 | —COCH$_3$ | H | H | H | H | H |
| C-13 | —SO$_3$—C$_6$H$_5$ | H | H | —NO$_2$ | H | H |

TABLE 4-continued

[Structure: naphthalene with Rᵃ, Rᵇ, Rᶜ, Rᵈ, Rᵉ, Rᶠ substituents; =N—SO₂—C₆H₄—CH₃ and N₂ groups]

| Compound No. | Rᵃ | Rᵇ | Rᶜ | Rᵈ | Rᵉ | Rᶠ |
|---|---|---|---|---|---|---|
| C-14 | H | H | H | H | —CO—C₆H₅ (phenyl ketone) | H |
| C-15 | H | H | H | —SO₂N(C₆H₁₃(n))₂ | H | H |
| C-16 | H | H | H | —CONH—C₆H₄—CH₃ | H | H |

TABLE 5

[Structure: naphthalene with Rᵃ, Rᵇ, Rᶜ, Rᵈ, Rᵉ, Rᶠ substituents; =N—SO₂—C₆H₄—CH₃ and N₂ groups]

| Compound No. | Rᵃ | Rᵇ | Rᶜ | Rᵈ | Rᵉ | Rᶠ |
|---|---|---|---|---|---|---|
| C-17 | H | H | H | —SO₃—C₆H₃(CH₃)₂ (2,4-dimethylphenyl sulfonate) | Br | H |
| C-18 | H | H | —SO₃—C₆H₅ | H | H | —SO₃—C₆H₅ |
| C-19 | H | H | —SO₃C₂H₅ | H | H | —SO₃C₂H₅ |
| C-20 | H | H | H | —NHCOC₄H₉(n) | H | H |
| C-21 | Br | H | H | —O—C₆H₅ | H | H |

TABLE 6
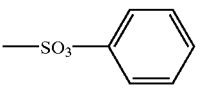
| Compound No. | $R^a$ | $R^b$ | $R^c$ | $R^d$ | $R^e$ | $R^f$ |
|---|---|---|---|---|---|---|
| D-1 | H | —SO$_3$—C$_6$H$_5$ | H | H | H | H |
| D-2 | H | H | —SO$_3$—C$_6$H$_4$—CH$_3$ (p) | H | H | H |
| D-3 | H | H | H | —SO$_3$—C$_6$H$_4$—CH$_3$ (p) | H | H |
| D-4 | H | H | H | —SO$_3$—(1-naphthyl) | H | H |
| D-5 | H | H | H | —SO$_3$—C$_6$H$_4$—OCH$_3$ | H | H |
| D-6 | H | H | H | —SO$_3$—(cyclohexyl) | H | H |
| D-7 | H | H | H | —SO$_3$C$_8$H$_{17}$(n) | H | H |
TABLE 7
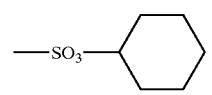
| Compound No. | $R^a$ | $R^b$ | $R^c$ | $R^d$ | $R^e$ | $R^f$ |
|---|---|---|---|---|---|---|
| D-8 | H | H | H | H | —SO$_3$—C$_6$H$_4$—CH$_3$ | H |
| D-9 | H | H | H | H | —SO$_3$—C$_6$H$_4$—C(CH$_3$)$_2$CH$_2$C(CH$_3$)$_3$ | H |
| D-10 | H | | Cl | H | H | H |

TABLE 7-continued
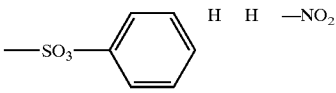
| Compound No. | $R^a$ | $R^b$ | $R^c$ | $R^d$ | $R^e$ | $R^f$ |
|---|---|---|---|---|---|---|
| D-11 | H | H | H | H | —SC$_{12}$H$_{25}$(n) | H |
| D-12 | —COCH$_3$ | H | H | H | H | H |
| D-13 | 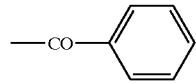 | H | H | —NO$_2$ | H | H |
| D-14 | H | H | H | H | 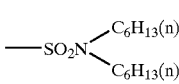 | H |
| D-15 | H | H | H | 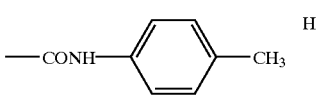 | H | H |
| D-16 | H | H | H | 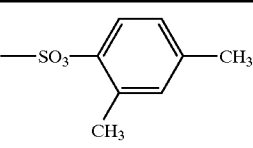 | H | H |
TABLE 8
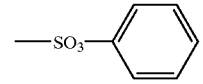
| Compound No. | $R^a$ | $R^b$ | $R^c$ | $R^d$ | $R^e$ | $R^f$ |
|---|---|---|---|---|---|---|
| D-17 | H | H | H | 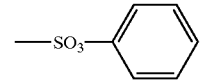 | Br | H |
| D-18 | H | H | 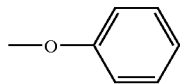 | H | —SO$_3$- (phenyl) | H |
| D-19 | H | H | —SO$_3$C$_2$H$_5$ | H | H | —SO$_3$C$_2$H$_5$ |
| D-20 | H | H | H | —NHCOC$_4$H$_9$(n) | H | H |
| D-21 | Br | H | H | —O-phenyl | H | H |

TABLE 9
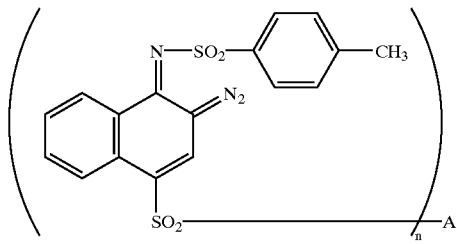

TABLE 10
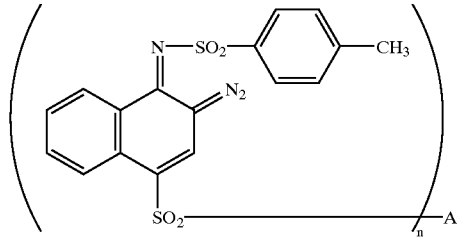

TABLE 11
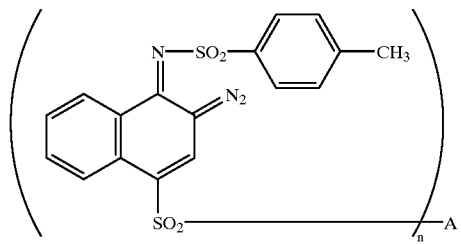
| | n | A |
|---|---|---|
| E-17 | 4 | 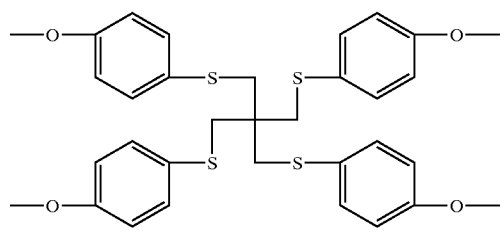 |
| E-18 | 6 | 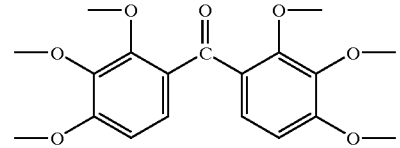 |
| E-19 | $1 \leq n = 2$ m (Also substitutable partially) | 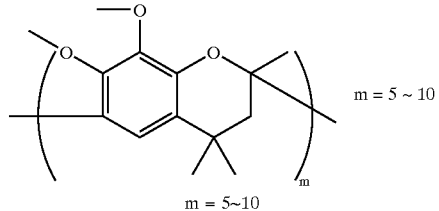 m = 5 ~ 10 |
| E-20 | $1 \leq n = m$ (Also substitutable partially) | 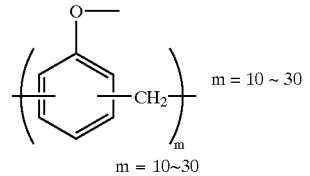 m = 10 ~ 30 |
TABLE 12
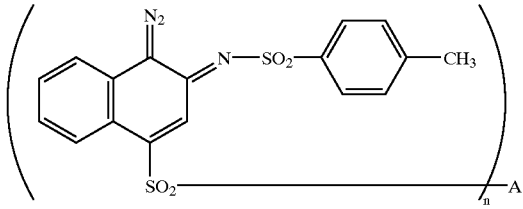
| | n | A |
|---|---|---|
| F-1 | 2 |  |

TABLE 12-continued
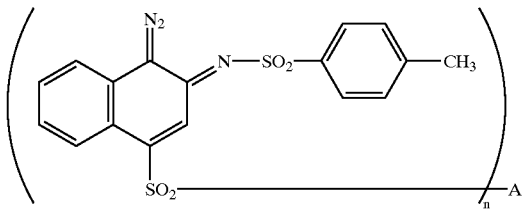
| | n | A |
|---|---|---|
| F-2 | 2 | 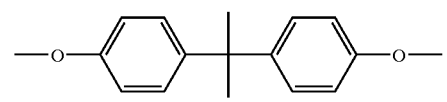 |
| F-3 | 2 | 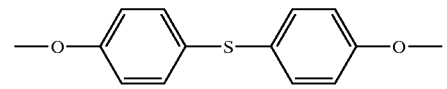 |
| F-4 | 2 | 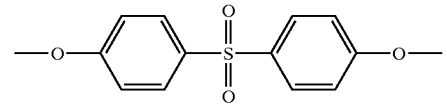 |
| F-5 | 2 | 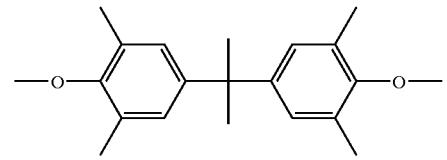 |
| F-6 | 2 | 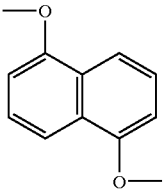 |
| F-7 | 2 |  |
| F-8 | 2 |  |
| F-9 | 2 |  |
| F-10 | 2 |  |

TABLE 13

| | n | A |
|---|---|---|
| F-11 | 2 | (structure) |
| F-12 | 2 | (structure) |
| F-13 | 2 | (structure) |
| F-14 | 3 | (structure) |
| F-15 | 3 | (structure) |
| F-16 | 3 | (structure) |

TABLE 14
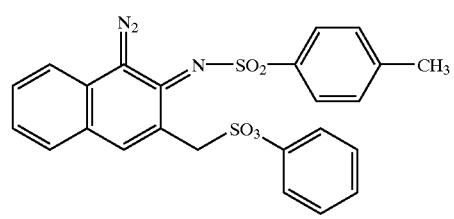
| | n | A |
|---|---|---|
| F-17 | 4 | (structure shown) |
| F-18 | 6 | (structure shown) |
| F-19 | 1 ≦ n = 2m (Also substitutable partially) | (structure shown) m = 5 ~ 10 |
| F-20 | 1 ≦ n = m (Also substitutable partially) | (structure shown) m = 10 ~ 30 |
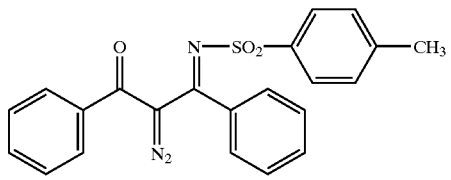
(G-1)
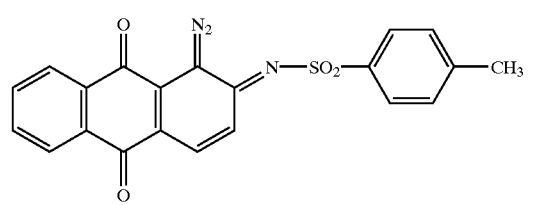
(G-2)
-continued
(G-3)
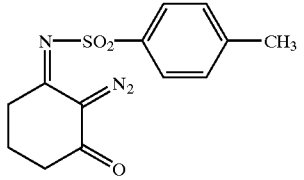
(G-4)

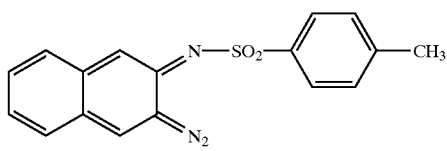
(G-5)
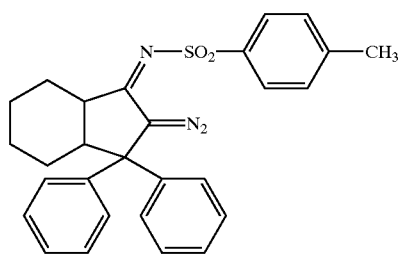
(G-6)
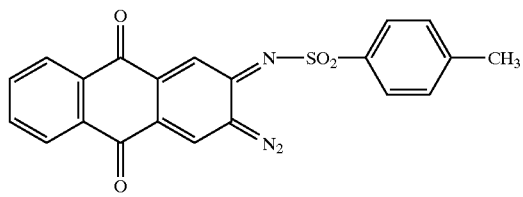
(G-7)
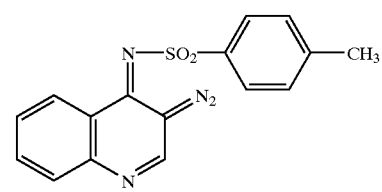
(G-8)
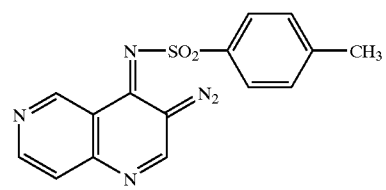
(G-9)
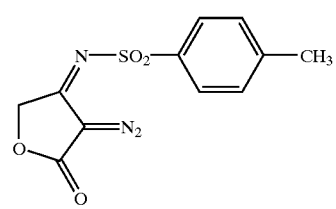
(G-10)
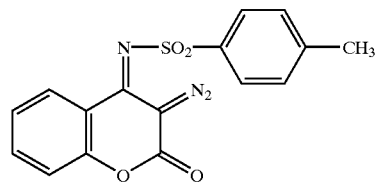
(G-11)
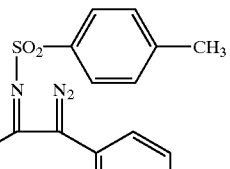
(G-12)
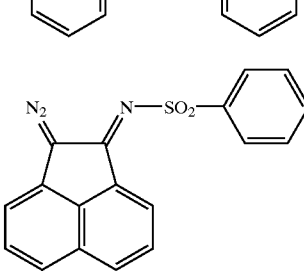
(G-13)
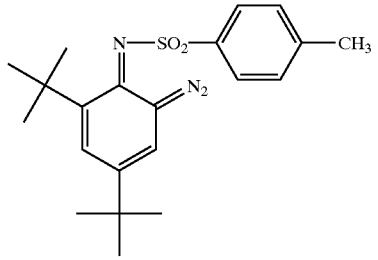
(G-14)
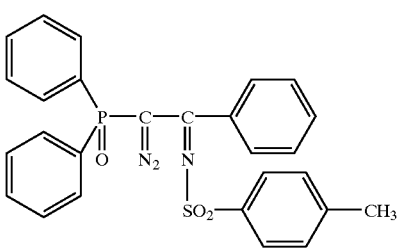
(G-15)
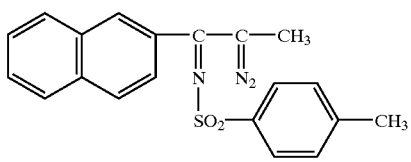
(G-16)
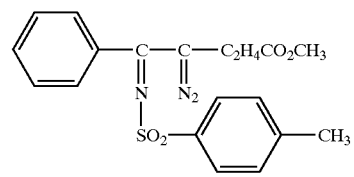
(G-17)
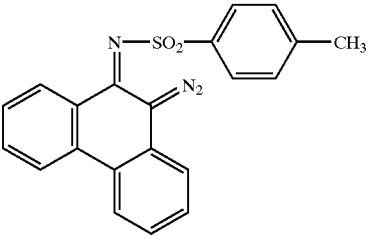
(G-18)

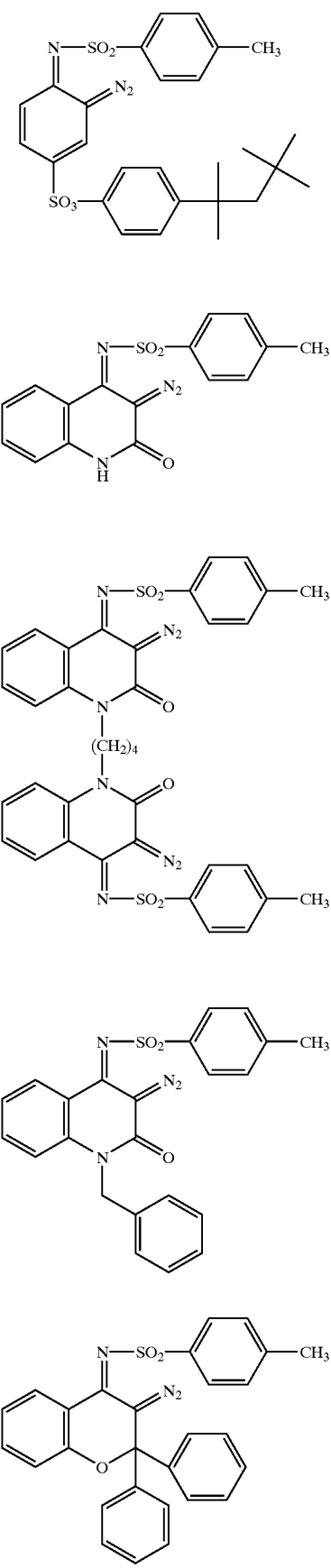
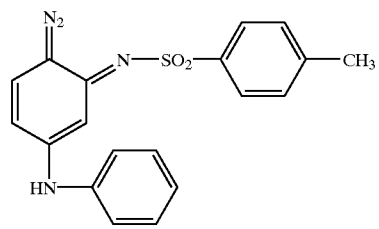
(G-19)
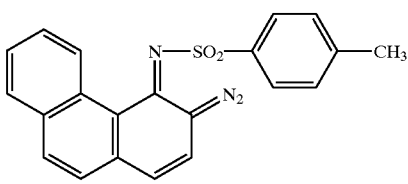
(G-24)
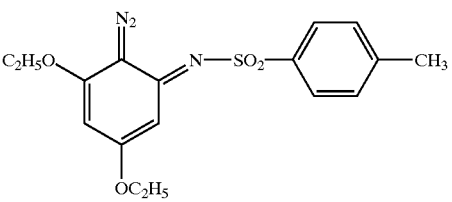
(G-25)
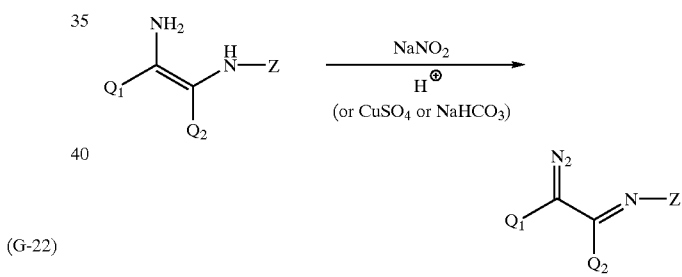
(G-26)
Such diazo compounds are commonly synthesized as represented in the following schemes.
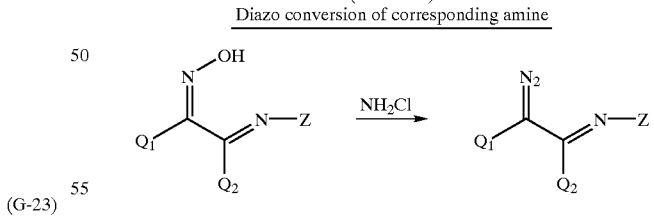
(Scheme 1)
Diazo conversion of corresponding amine
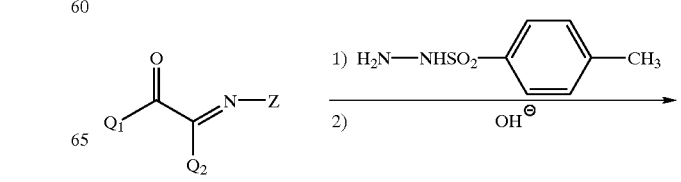
(Scheme 2)
Forster reaction of corresponding oxine

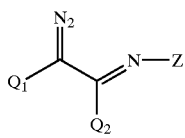

(Scheme 3) Bamford-Stevens reaction of corresponding ketone

Scheme 1 is the most commonly used of these.

Details of the aforementioned methods are given in Chapters 14, 15, and 17 in particular in *The Chemistry of Functional Groups: The Chemistry of Diazonium and Diazo Groups*, Parts 1 and 2, by Saul Patai, John Wiley & Sons (1978).

The diazo compounds of the present invention are particularly suitable for positive lithographic printing materials for heat mode printing in which the plates have a low moisture content during development.

(B) Water-Insoluble and Alkaline Water-Soluble Polymers

A polymer (B) that is water-insoluble but alkaline water-soluble (alkaline water-soluble polymer), that is, a homopolymer with acidic groups in the polymer main chain and/or side chains, a copolymer thereof, or a mixture thereof, is used as the binder polymer in the positive photosensitive composition of the present invention. The positive photosensitive composition of the present invention can thus be developed in an alkaline developer.

Those with acidic groups in the polymer main chain and/or side chains in (1) through (6) below are preferred for the sake of dissolution in alkaline developers and the ability to control such dissolution.

(1) phenol groups (—Ar—OH)
(2) sulfonamide groups (—SO$_2$NH—R)
(3) substituted sulfonamide acid groups (hereinafter referred to as "active imide groups") (—SO$_2$NHCOR, —SO$_2$NHSO$_2$R, —CONHSO$_2$R)
(4) carboxylic acid groups (—CO$_2$H)
(5) sulfonic acid groups (—SO$_3$H)
(6) phosphoric acid groups (—OPO$_3$H$_2$)

In (1) and (6) above, Ar represents an optionally substituted divalent aryl linkage, and R represents an optionally substituted hydrocarbon group.

Alkaline water-soluble polymers with (1) phenol groups, (2) sulfonamide groups, and (3) active imide groups are preferred among the alkaline water-soluble polymers with acidic groups selected from (1) through (6) above. Alkaline water-soluble polymers having (1) phenol groups or (2) sulfonamide groups are ideal in terms of solubility in alkaline developers, development latitude, and adequately preserved film strength.

The following are examples of alkaline water-soluble polymers with acidic groups selected from (1) through (6) above.

Examples of alkaline water-soluble polymers having (1) phenol groups include condensation polymers of phenol and formaldehyde, condensation polymers of m-cresol and formaldehyde, condensation polymers of p-cresol and formaldehyde, condensation polymers of m-/p-cresol mixtures and formaldehyde, condensation polymers of phenol and cresol (m-, p-, or m-/p-mixtures) and formaldehyde, and similar novolak resins, as well as condensation polymers of pyrogallol and acetone. Alternatively, copolymers comprising the copolymers of compounds having phenol groups in the side chains can also be used.

Examples of compounds with phenol groups include phenol group-containing acrylamides, methacrylamides, acrylate esters, methacrylate esters, and hydroxystyrene.

Specific examples include N-(2-hydroxyphenyl)acrylamide, N-(3-hydroxyphenyl)acrylamide, N-(4-hydroxyphenyl)acrylamide, N-(2-hydroxyphenyl)methacrylamide, N-(3-hydroxyphenyl)methacrylamide, N-(4-hydroxyphenyl)methacrylamide, o-hydroxyphenylacrylate, m-hydroxyphenylacrylate, p-hydroxyphenylacrylate, o-hydroxyphenylmethacrylate, m-hydroxyphenylmethacrylate, p-hydroxyphenylmethacrylate, o-hydroxystyrene, m-hydroxystyrene, p-hydroxystyrene, 2-(2-hydroxyphenyl)ethylacrylate, 2-(3-hydroxyphenyl)ethylacrylate, 2-(4-hydroxyphenyl)ethylacrylate, 2-(2-hydroxyphenyl)ethylmethacrylate, 2-(3-hydroxyphenyl)ethylmethacrylate, and 2-(4-hydroxyphenyl)ethylmethacrylate.

The weight-average molecular weight of the polymer is between $5.0 \times 10^2$ to $2.0 \times 10^4$, and a number average molecular weight of $2.0 \times 10^2$ to $1.0 \times 10^4$ is preferred for the sake of image formation. These polymers may be used alone or in combinations of two or more. When combined, condensation polymers of t-butylphenol and formaldehyde such as that described in U.S. Pat. No. 4,123,279, and condensation polymers of formaldehyde and phenols with $C_3$ to $C_8$ alkyl groups as substituents, such as condensation polymers of octylphenol and formaldehyde, may also be used.

Examples of alkaline water-soluble polymers having (2) sulfonamide groups include polymers comprising minimum structural units derived from compounds having sulfonamide groups as a primary constituent. Examples of such compounds include compounds having at least one each of a sulfonamide group with at least one hydrogen atom bonded to a nitrogen atom, and a polymerizable unsaturated group, per molecule.

Preferred among these are low molecular weight compounds having an acryloyl group, allyl group, or vinyloxy group and a substituted or mono-substituted aminosulfonyl group or substituted sulfonylimino group per molecule. Examples include the following compounds represented by General Formulas 2 through 6.

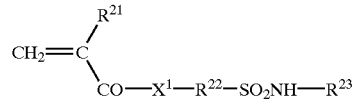

General Formula 2

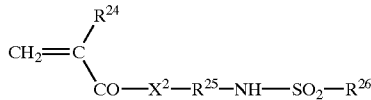

General Formula 3

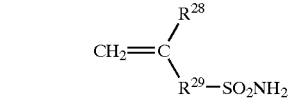

General Formula 4

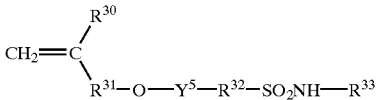

General Formula 5

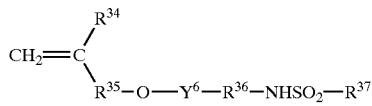

General Formula 6

(Where $X^1$ and $X^2$ each independently represent —O— or —NR$^{27}$—. $R^{21}$ and $R^{24}$ each independently represent a hydrogen atom or —CH$_3$. $R^{22}$, $R^{25}$, $R^{29}$, $R^{32}$, and $R^{36}$ each independently represent an optionally substituted $C_1$ to $C_{12}$ alkylene group, cycloalkylene group, arylene group, or aralkylene group. $R^{23}$, $R^{27}$, and $R^{33}$ each independently represent a hydrogen atom, an optionally substituent-bearing $C_1$ to $C_{12}$ alkyl group, cycloalkyl group, aryl group, or aralkyl group. $R^{26}$ and $R^{37}$ each independently represent an optionally substituent-bearing $C_1$ to $C_{12}$ alkyl group, cycloalkyl group, aryl group, or aralkyl group. $R^{28}$, $R^{30}$, and $R^{34}$ each independently represent a hydrogen atom or —$CH_3$. $R^{31}$ and $R^{35}$ each independently represent a $C_1$ to $C_{12}$ alkylene group, cycloalkylene group, arylene group, or aralkylene group which may have a substituent or a single bond. $Y^5$ and $Y^6$ each independently represent a single bond or —CO—.)

The use of m-aminosulfonylphenyl methacrylate, N-(p-aminosulfonylphenyl) methacrylamide, N-(p-aminosulfonylphenyl) acrylamide and the like is preferred among the compounds represented by General Formulas 2 through 6 in the positive photosensitive composition of the present invention.

Examples of alkaline water-soluble polymers having (3) active imide groups include polymers comprising minimum structural units derived from compounds having active imide groups as a primary constituent. Examples of such compounds include compounds having at least one each of an active imide group represented by the following structural formula and a polymerizable unsaturated group per molecule.

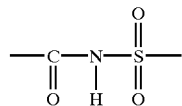

Specifically, the use of N-(p-toluenesulfonyl) methacrylamide, N-(p-toluenesulfonyl)acrylamide, and the like is preferred.

Examples of alkaline water-soluble polymers having (4) carboxylic acid groups include polymers comprising as a primary substituent minimum structural units derived from compounds having at least one each of a carboxylic acid group and a polymerizable unsaturated group per molecule.

Examples of alkaline water-soluble polymers having (5) sulfonic acid groups include polymers comprising as a primary substituent minimum structural units derived from compounds having at least one each of a sulfonic acid group and a polymerizable unsaturated group per molecule.

Examples of alkaline water-soluble polymers having (6) phosphoric acid groups include polymers comprising as a primary substituent minimum structural units derived from compounds having at least one each of a phosphoric acid group and a polymerizable unsaturated group per molecule.

Preferred among the aforementioned alkaline water-soluble polymers are alkaline water-soluble polymers having (1) phenolic hydroxyl groups because of the ability to obtain potent hydrogen bonding interaction between specific functional groups —X—Y—Z of such phenolic compounds.

The minimum structural units having acidic groups selected from (1) through (6) above forming the alkaline water-soluble polymer used in the positive photosensitive composition of the present invention need not necessarily be of only one kind. Those comprising the copolymerization of two or more kinds of minimum structural units with the same acidic groups or two or more kinds of minimum structural units with different acidic groups can be used.

Examples of copolymerization methods which can be used include conventionally known graft copolymerization, block copolymerization, and random copolymerization.

Such copolymers preferably include 10 mol % or more, and more preferably 20 mol % or more, of compounds with acidic groups selected from (1) through (6). Less than 10 mol % usually will not result in satisfactory improvement in development latitude.

When these compounds are copolymerized into copolymers in the present invention, other compounds which do not contain the aforementioned acidic groups in (1) through (6) can also be used. The compounds in (m1) through (m12) below are examples of other compounds without the acidic groups in (1) through (6).

(m1) Examples include acrylic acid esters and methacrylic acid esters having aliphatic hydroxyl groups, such as 2-hydroxyethylacrylate and 2-hydroxyethylmethacrylate.

(m2) Examples include alkyl acrylates such as methyl acrylate, ethyl acrylate, propyl acrylate, butyl acrylate, amyl acrylate, hexyl acrylate, octyl acrylate, benzyl acrylate, 2-chloroethyl acrylate, glycidyl acrylate, and N-dimethylaminoethyl acrylate.

(m3) Examples include alkyl methacrylates such as methyl methacrylate, ethyl methacrylate, propyl methacrylate, butyl methacrylate, amyl methacrylate, hexyl methacrylate, cyclohexyl methacrylate, benzyl methacrylate, 2-chloroethyl methacrylate, glycidyl methacrylate, and N-dimethylaminoethyl methacrylate.

(m4) Examples include acrylamides and methacrylamides such as acrylamide, methacrylamide, N-methylol acrylamide, N-ethyl acrylamide, N-hexyl methacrylamide, N-cyclohexyl acrylamide, N-hydroxyethyl acrylamide, N-phenyl acrylamide, N-nitrophenyl acrylamide, and N-ethyl-N-phenyl acrylamide.

(m5) Examples include vinyl ethers such as ethyl vinyl ether, 2-chloroethyl vinyl ether, hydroxyethyl vinyl ether, propyl vinyl ether, butyl vinyl ether, octyl vinyl ether, and phenyl vinyl ether.

(m6) Examples include vinyl esters such as vinyl acetate, vinyl chloroacetate, vinyl butyrate, and vinyl benzoate.

(m7) Examples include styrenes such as styrene, α-methylstyrene, methylstyrene, and chloromethylstyrene.

(m8) Examples include vinyl ketones such as methyl vinyl ketone, ethyl vinyl ketone, propyl vinyl ketone, and phenyl vinyl ketone.

(m9) Examples include olefins such as ethylene, propylene, isobutylene, butadiene, and isoprene.

(m10) Examples include N-vinyl pyrrolidone, N-vinyl carbazole, 4-vinyl pyridine, acrylonitrile, and methacrylonitrile.

(m11) Examples include unsaturated imides such as maleimide, N-acryloyl acrylamide, N-acetyl methacrylamide, N-propionyl methacrylamide, and N-(p-chlorobenzoyl)methacrylamide.

(m12) Examples include unsaturated carboxylic acids such as acrylic acid, methacrylic acid, maleic anhydride, and itaconic acid.

The alkaline water-soluble polymer used in the positive photosensitive composition of the present invention, whether a homopolymer or copolymer, should have a weight-average molecular weight of $1.0 \times 10^3$ to $2.0 \times 10^5$, and a number average molecular weight of $5.0 \times 10^2$ to $1.0 \times 10^5$ for the sake of sensitivity and development latitude. The distribution (weight-average molecular weight/number average molecular weight) is preferably between 1.1 and 10.

When a copolymer is used in the present invention, the blend weight ratio between the minimum structural units derived from compounds having acidic groups selected from (1) through (6) above forming the main chain and/or side chains, and the other minimum structural units without the acidic groups of (1) through (6) forming a part of the main chain and/or side chains, should range between 50:50 and 5:95, and even more preferably between 40:60 and 10:90.

The aforementioned alkaline water-soluble polymers may be used individually or in combinations of two or more. They should be used within a range of between 30 and 99 wt %, preferably between 40 and 95 wt %, and even more preferably between 50 and 90 wt %, of the total solids of the positive photosensitive composition.

When the alkaline water-soluble polymer is used in an amount of less than 30 wt %, the printing layer durability tends to deteriorate, whereas more than 99 wt % tends to result in lower sensitivity and durability.

Novolak resins are described below.

Examples of novolak resins suitable for use in the present invention include condensation polymers of phenol and formaldehyde, condensation polymers of m-cresol and formaldehyde, condensation polymers of p-cresol and formaldehyde, condensation polymers of m-/p-cresol mixtures and formaldehyde, condensation polymers of phenol and cresol (m-, p-, or m-/p-mixtures) and formaldehyde, and similar novolak resins, as well as condensation polymers of pyrogallol and acetone. Alternatively, copolymers of monomers having phenol groups in the side chains can also be used.

Examples of solvents which can be used during the synthesis of the alkaline water-soluble polymers used in the present invention include tetrahydrofuran, ethylene dichloride, cyclohexane, methyl ethyl ketone, acetone, methanol, ethanol, ethylene glycol monomethyl ether, ethylene glycol monoethyl ether, 2-methoxyethyl acetate, diethylene glycol dimethyl ether, 1-methoxy-2-propanol, 1-methoxy-2-propyl acetate, N,N-dimethyl formamide, N,N-dimethyl acetamide, toluene, ethyl acetate, methyl acetate, ethyl lactate, dimethyl sulfoxide, and water. These solvents may be used alone or in combinations of two or more.

(C) Infrared Absorbents

Various pigments or dyes can be used as infrared absorbents in the present invention.

Examples of pigments include commercially available pigments and pigments listed in the Color Index (C.I.) Manual, Saishin Ganryo Binran [*Recent Pigments Manual*] (ed. by Nihon Ganryo Gijutsu Kyokai (1977)), Saishin Ganryo Oyo Gijutsu [*Recent Pigment Applications and Techniques*] (published by CMC (1986 ed.)), and Insatsu Inki Gijutsu [*Printing Ink Techniques*] (published by CMC (1984)).

Types of pigments include black pigments, yellow pigments, orange pigments, brown pigments, red pigments, violet pigments, blue pigments, green pigments, fluorescent pigments, metallic powder pigments, and other polymer bonded dyes. Specific examples which can be used include insoluble azo pigments, azo lake pigments, condensed azo pigments, chelate azo pigments, phthalocyanine pigments, anthraquinone pigments, perylene and perinone pigments, thioindigo pigments, quinacridone pigments, dioxazine pigments, isoindolinone pigments, quinophthalone pigments, printing lake pigments, azine pigments, nitroso pigments, nitro pigments, natural pigments, fluorescent pigments, inorganic pigments, and carbon black.

These pigments can be used with or without surface treatment. Methods of surface treatment include methods for coating surfaces with resin or wax, methods for applying surfactants, and methods for allowing reactive substances (such as silane coupling agents, epoxy compounds, and polyisocyanates) to bond to the surface of the pigments. The aforementioned surface treatments are described in Kinzoku Sekken no Seishitsu to Oyo [*Metal Soap Properties and Applications*] (published by Koshobo), Insatsu Inki Gijutsu [*Printing Ink Techniques*] (published by CMC (1984)), and Saishin Ganryo Oyo Gijutsu [*Recent Pigment Applications and Techniques*] (published by CMC (1986 ed.)).

The pigment particle diameter preferably ranges between 0.01 and 10 $\mu$m, more preferably between 0.05 and 1 $\mu$m, and even more preferably between 0.1 and 1 $\mu$m. A pigment particle diameter of less than 0.01 $\mu$m is undesirable in terms of the stability of the dispersed material in the photosensitive layer coating solution, while a particle diameter greater than 10 $\mu$m is undesirable in terms of the uniformity of the photosensitive layer.

Common dispersion techniques employed in the manufacture of ink, toner, and the like can be used to disperse the pigment. Examples of dispersion devices include ultrasonic dispersers, sand mills, attritors, pearl mills, super mills, ball mills, impellers, disperses, KD mills, colloid mills, dynatrons, three-roll mills, and pressure kneaders. Details are available in Saishin Ganryo Oyo Gijutsu [*Recent Pigment Applications and Techniques*] (published by CMC (1986 ed.)).

Commercially available and well-known dyes given in documents such as Senryo Binran [*Dye Manual*] (ed. Yuki Gosei Kagaku Kyokai (1970 ed.)) can be used. Specific examples include azo dyes, metal complex salt azo dyes, pyrazolone azo dyes, naphthoquinone dyes, anthraquinone dyes, phthalocyanine dyes, carbonium dyes, quinoneimine dyes, methine dyes, squarylium dyes, and metal thiolate complexes.

Of these pigments and dyes, those that absorb infrared rays and near infrared rays are preferred because they are suitable for use with lasers emitting infrared or near infrared rays.

Carbon black is preferably used as the pigment absorbing such infrared or near infrared rays. Examples of dyes absorbing infrared and near infrared rays include the cyanine dyes given in Japanese Patent Application Laid-Open (JP-A) Nos.58-125246, 59-84356, 59-202829, and 60-78787, the methine dyes given in Japanese Patent Application Laid-Open (JP-A) Nos.58-173696, 58-181690, and 58-194595, the naphthoquinone dyes given in Japanese Patent Application Laid-Open (JP-A) Nos.58-112793, 58-224793, 59-48187, 59-73996, and 60-52940, and 60-63744, the squarylium dyes given in Japanese Patent Application Laid-Open (JP-A) No. 58-112792, and the cyanine dyes given in UK Patent 434,875.

The infrared absorbing sensitizer noted in U.S. Pat. No. 5,156,938 is also suitable for use as a dye. Particularly desirable for use are the substituted arylbenzo(thio)pyrylium salts in U.S. Pat. No. 3,881,924, the trimethine thiapyrylium salts in Japanese Patent Application Laid-Open (JP-A) No.57-142645 (U.S. Pat. No. 4,327,169), the pyrylium compounds in Japanese Patent Application Laid-Open (JP-A) Nos.58-181051, 58-220143, 59-41363, 59-84248, 59-84249, 59-146063, and 59-146061, the cyanine dyes in Japanese Patent Application Laid-Open (JP-A) No.59-216146, the pentamethine thiopyrylium salts and the like in U.S. Pat. No. 4,283,475 or the pyrylium compounds Epolight III-178, III-130, and III-125 disclosed in Japanese Examined Patent Applications (Kokoku) 5-13514 and 5-19702.

Other particularly desirable examples of dyes include the infrared absorbing dyes given under Formulas I and II in U.S. Pat. No. 4,756,993.

The dyes and pigments are preferably added in an amount of between 0.01 and 50 wt %, and more preferably between 0.1 and 10 wt %, relative to the total solids of the photosensitive composition. Dyes are even more preferably added in an amount of between 0.5 and 10 wt %, while pigments are even more preferably added in an amount of between 1.0 and 10 wt %, to the photosensitive composition. Adding less than 0.01 wt % pigment or dye results in lower sensitivity, whereas adding more than 50 wt % will stain the areas with no images during printing.

The dye or pigment may be added to the same layer as the other components, or it may be added to a separate layer. Infrared or near infrared absorbing dyes or pigments are preferred among the above. The dyes and pigments may be used in combinations of two or more.

Other Components

Various additives can be added to the positive photosensitive composition of the present invention. For example, onium salts, aromatic sulfone compounds, aromatic sulfonic acid ester compounds and the like have action as thermally decomposing materials, and can thus be added to improve the dissolution inhibition properties of the image areas in the developer.

Examples of onium salts include diazonium salts, ammonium salts, phosphonium salts, iodonium salts, sulfonium salts, selenonium salts, and arsonium salts. Examples of onium salts suitable for use in the present invention include the diazonium salts in S. I. Schlesinger, Photogr. Sci. Eng., 18, 387 (1974), T. S. Bal et al, Polymer, 21, 423 (1980), and Japanese Patent Application Laid-Open (JP-A) No.5-158230, the ammonium salts in U.S. Pat. Nos. 4,069,055 and 4,069,056, and Japanese Patent Application Laid-Open (JP-A) No.3-140140, the phosphonium salts in D. C. Necker et al, Macromolecules, 17, 2468 (1984), C. S. Wen et al, Teh, Proc. Conf. Rad. Curing ASIA, p. 478, Tokyo, Oct (1988), and U.S. Pat. Nos. 4,069,055 and 4,069,056, the iodonium salts in J. V. Crivello et al, Macromolecules, 10 (6), 1307 (1977), Chem. & Eng. News, Nov. 28, p. 31 (1988), European Patent 104,143, U.S. Pat. Nos. 339,049 and 410,201, and Japanese Patent Application Laid-Open (JP-A) Nos. 2-150848 and 2-296514, sulfonium salts in J. V. Crivello et al, Polymer J., 17, 73 (1985), J. V. Crivello et al, J. Org. Chem., 43, 3055 (1978), W. R. Watt et. al, J. Polymer Sci., Polymer Chem. Ed., 22, 1789 (1984), J. V. Crivello et al, Polymer Bull., 14, 279 (1985), J. V. Crivello et al, Macromolecules, 14 (5), 1141 (1981), J. V. Crivello et al, J. Polymer Sci., Polymer Chem. Ed., 17, 2877 (1979), European Patents 370,693, 233, 567, 297,443, and 297,442, U.S. Pat. Nos. 4,933,377, 3,902,114, 410,201, 339,049, 4,760, 013, 4,734,444, and 2,833,827, and German Patents 2,904, 626, 3,604,580, and 3,604,581, the selenonium salts in J. V. Crivello et al, Macromolecules, 10 (6), 1307 (1977), and J. V. Crivello et al. J. Polymer Sci., Polymer chem. Ed., 17, 1047 (1979), and the arsonium salts in C. S. Wen et al, Teh, Proc. Conf. Rad. Curing ASIA, p. 478, Tokyo, October (1988).

Examples of counterions for the aforementioned onium salts include tetrafluoroboric acid, hexafluorophosphoric acid, triisopropylnaphthalenesulfonic acid, 5-nitro-o-toluenesulfonic acid, 5-sulfosalicylic acid, 2,5-dimethylbenzenesufonic acid, 2,4,6-trimethylbenzenesulfonic acid, 2-nitrobenzenesulfonic acid, 3-chlorobenzenesulfonic acid, 3-bromobenzenesulfonic acid, 2-fluorocaprylnaphthalenesulfonic acid, dodecylbenzenesulfonic acid, 1-naphthol-5-sulfonic acid, 2-methoxy-4-hydroxy-5-benzoyl-benzenesulfonic acid, and para-toluenesulfonic acid.

Particularly preferred among these are hexafluorophosphoric acid, triisopropylnaphthalenesulfonic acid, and 2,5-dimethylbenzenesufonic acid.

The onium salts are preferably added in an amount of between 1 and 50 wt %, more preferably between 5 and 30 wt %, and even more preferably between 10 and 30 wt %.

Dyes having substantial absorption in the visible light range can be used as colorants for images. Liposoluble dyes and basic dyes are examples of favorable dyes.

Specific examples include Direct Yellow #101, Oil Yellow #103, Oil Pink #312, Oil Green BG, Oil Blue BOS, Oil Blue #603, Oil Black BY, Oil Black BS, Oil Black T-505 (by Orient Kagaku Kogyo), Victoria Pure Blue, crystal violet (CI 42555), methyl violet (CI 42535), ethyl violet, rhodamine B (CI 145170 B), malachite green (CI 42000), methylene blue (CI 52015), Eisen Spiron Blue C-RH (by Hodogaya Chemical), and the like, as well as the dyes given in Japanese Patent Application Laid-Open (JP-A) No.62-293247.

Such dyes are preferably added to distinguish between areas where images are and are not formed after imaging. The amount to add is preferably 0.01 to 10 wt % relative to the total solids of the photosensitive composition.

Cyclic acid anhydrides, phenols, and organic acids can be added to further improve sensitivity. Examples of cyclic acid anhydrides include those given in U.S. Pat. No. 4,115,128, such as phthalic anhydride, tetrahydrophthalic anhydride, hexahydrophthalic anhydride, 3,6-endoxy-$\Delta^4$-tetrahydrophthalic anhydride, tetrachlorophthalic anhydride, maleic anhydride, chloromaleic anhydride, α-phenylmaleic acid anhydride, succinic anhydride, and pyromellitic anhydride.

Examples of phenols include bisphenol A, p-nitrophenol, p-ethoxyphenol, 2,4,4'-trihydroxybenzophenone, 2,3,4-trihydroxybenzophenone, 4-hydroxybenzophenone, 4,4',4"-tridydroxytriphenylmethane, and 4,4',3",4"-tetrahydroxy-3,5,3', 5'-tetramethyltriphenylmethane.

Examples of organic acids include those given in Japanese Patent Application Laid-Open (JP-A)Nos.60-88942 and 2-96755, such as sulfonic acids, sulfinic acids, alkylsulfuric acids, phosphonic acids, phosphate esters, and carboxylic acids. Specific examples include p-toluenesulfonic acid, dodecylbenzenesulfonic acid, p-toluenesulfinic acid, ethylsulfuric acid, phenylphosphonic acid, phenylphosphinic acid, phenyl phosphate, diphenyl phosphate, benzoic acid, isophthalic acid, adipic acid, p-toluylic acid, 3,4-dimethoxybenzoic acid, phthalic acid, terephthalic acid, 4-cyclohexene-1,2-dicarboxylic acid, erucic acid, lauric acid, n-undecanoic acid, and ascorbic acid.

The proportion of the aforementioned cyclic acid anhydrides, phenols, and organic acids in the printing plate material is preferably between 0.05 and 20 wt %, more preferably between 0.1 and 15 wt %, and even more preferably between 0.1 and 10 wt %.

Nonionic surfactants such as those given in Japanese Patent Application Laid-Open (JP-A) Nos.62-251740 and 3-208514 and amphoteric surfactants such as those given in Japanese Patent Application Laid-Open (JP-A) Nos.59-121044 and 4-13149 can also be added to the photosensitive composition of the present invention in order to improve treatment stability for developing conditions.

Specific examples of nonionic surfactants include sorbitan tristearate, sorbitan monopalmitate, sorbitan trioleate, monoglyceride stearate, and polyoxyethylene nonylphenyl ether. Examples of amphoteric surfactants include alkyl di(aminoethyl) glycine, alkylpolyaminoethyl glycine hydrochloride, 2-alkyl-N-carboxyethyl-N-hydroxyethylimidazolinium betaine, N-tetradecyl-N,N-betaine types (such as Amorgen K, trademark by Dai'ichi Kogyo).

The proportion of the aforementioned nonionic surfactants and amphoteric surfactants in the photosensitive composition is preferably between 0.05 and 15 wt %, and more preferably between 0.1 and 5 wt %.

Pigments or dyes serving as image colorants or print-out agents for obtaining visible images immediately after heating during exposure can be added to the positive photosensitive composition of the present invention.

Examples of typical print-out agents include combinations of compounds that release acid upon being heated during exposure (acid-releasing agents) and organic dyes capable for forming salts. Specific examples include combinations of o-naphthoquinonediazide-4-sulfonic acid halogenides and salt-forming organic dyes such as those given in Japanese Patent Application Laid-Open (JP-A) Nos.50-36209 and 53-8128, and combinations of trihalomethyl compounds and salt-forming organic dyes such as those given in Japanese Patent Application Laid-Open (JP-A) Nos. 53-36223, 54-74728, 60-3626, 61-143748, 61-151644, and 63-58440. Examples of such trihalomethyl compounds include oxazole compounds and triazine compounds, both of which provide excellent stability over time and distinct printed images.

Epoxy compounds, vinyl ether compounds, the phenol compounds with hydroxymethyl groups or alkoxymethyl groups in Japanese Patent Application 7-18120, and the cross-linked compounds having action in inhibiting alkali dissolution in Japanese Patent Application 9-328937 are preferably added for the sake of storage stability.

Plasticizers can also be added to the positive photosensitive composition of the present invention as needed to make the coated film more flexible and the like. Preferred examples include butylphthalyl, polyethylene glycol, tributyl citrate, diethyl phthalate, dibutyl phthalate, dihexyl phthalate, dioctyl phthalate, tricresyl phosphate, tributyl phosphate, trioctyl phosphate, tetrahydrofurfuryl oleate, and acrylic acid or methacrylic acid oligomers and polymers.

Surfactants such as the fluorine surfactants in Japanese Patent Application Laid-Open (JP-A) No.62-170950 can be added to the positive photosensitive composition of the present invention to improve the coating properties. They are added in an amount of between 0.01 and 1 wt %, and preferably between 0.05 and 0.5 wt %, of the total photosensitive composition.

The positive photosensitive composition of the present invention can be produced by the following common methods for producing photosensitive compositions.

Photosensitive compositions are usually produced by dissolving the aforementioned components in a solvent and then spreading the resulting solution on a suitable support. Examples of solvents used in this case include, but are not limited to, ethylene dichloride, cyclohexanone, methyl ethyl ketone, methanol, ethanol, propanol, ethylene glycol monomethyl ether, 1-methoxy-2-propanol, 2-methoxyethyl acetate, 1-methoxy-2-propyl acetate, dimethoxyethane, methyl lactate, ethyl lactate, N,N-dimethyl acetamide, N,N-dimethyl formamide, tetramethyl urea, N-methyl pyrrolidone, dimethyl sulfoxide, sulfolane, γ-butyrolactone, toluene, and water. Such solvents can be used alone or in combination. The concentration of the above components in the solvent (total solids including additives) is preferably between 1 and 50 wt %. The coated amount (solids) on the support after drying will vary, depending on the application, but in general is preferably between 0.5 and 5.0 g/m$^2$ when used for photosensitive lithography.

Various coating methods can be employed, such as bar coater coating, rotary coating, spray coating, curtain coating, dip coating, air knife coating, blade coating, and roll coating. Although the apparent sensitivity increases as the coated amount decreases, the coating properties of the photosensitive film also decrease. The coated layer is the photosensitive layer of the photosensitive composition.

The support is a dimensionally stable material in the form of a sheet, such as paper, paper laminated with plastic (such as polyethylene, polypropylene, and polystyrene), metal sheets (such as aluminum, zinc, and copper), plastic films (such as cellulose diacetate, cellulose triacetate, cellulose propionate, cellulose butyrate, cellulose acetate butyrate, cellulose nitrate, polyethylene terephthalate, polyethylene, polystyrene, polypropylene, polycarbonate, and polyvinyl acetal), and paper or plastic films with metals such as the above laminated or deposited thereon.

Polyester films or aluminum sheets are preferred as the support used in the present invention. of these, relatively inexpensive aluminum sheets with good dimensional stability are especially preferred. Suitable aluminum sheets are pure aluminum sheets, alloy sheets comprising aluminum as the main component and minute amounts of other elements, as well as plastic films with aluminum laminated or deposited thereon. Examples of different elements which can be incorporated in aluminum alloys include silicon, iron, manganese, copper, magnesium, chromium, zinc, bismuth, nickel, and titanium. The content of such different elements in alloys should be, at most, no more than 10 wt %. Although pure aluminum is especially desirable in the present invention, trace amounts of other elements may be included since it is technically difficult, in terms of refining, to produce entirely pure aluminum. The composition of aluminum sheets suitable for the present invention is not specified. Aluminum sheets of conventional well-known materials are suitable for use.

The aluminum sheets used in the present invention are about 0.1 to 0.6 mm thick, preferably 0.15 to 0.4 mm thick, and even more preferably 0.2 to 0.3 mm thick.

Although aluminum sheets may undergo surface roughening, the surface can first be degreased with a surfactant, organic solvent, alkaline aqueous solution, or the like to remove rolling oil from the surface, if desired, before surface roughening.

Various methods can be used for surface roughening on aluminum sheets. Examples include mechanical roughening methods, electrochemical surface dissolving roughening methods, and chemically selective surface dissolving methods. Examples of mechanical methods which can be used include well known methods such as ball polishing methods, brush polishing methods, blast polishing methods, and buff polishing methods. Electrochemical methods of roughening include methods carried out with the use of AC or DC in hydrochloric acid or nitric acid electrolytic solution. Methods combining these two, such as that disclosed in Japanese Patent Application Laid-Open (JP-A) No.54-63902, can also be used.

Aluminum sheets which have undergone such surface roughening treatment may undergo alkali etching treatment and neutralization treatment as needed, and then anodic oxidation treatment to improve surface water retention or friction resistance as desired. various electrolytes for forming porous oxidation films can be used as the electrolyte in the anodic oxidation treatment of the aluminum sheets. Sulfuric acid, phosphoric acid, oxalic acid, chromic acid, or mixtures thereof are commonly used. The concentration of the electrolyte can be determined as needed depending on the type of electrolyte.

The conditions of anodic oxidation vary according to the electrolyte that is used and thus cannot be specified as a matter of absolute principle, but the electrolyte concentration is generally 1 to 80 wt % solution, the temperature of 5 to 70° C., the current density is 5 to 60 A/dm², the voltage is 1 to 100 V, and the electrolysis time is 10 seconds to 5 minutes. An anodic oxidation film of less than 1.0 g/m² will result in unsatisfactory print durability and tends to result in what is referred to as damage stains, where damage to the parts of the photosensitive composition in the areas where no images are formed can result in ink adhering to the damaged portions during printing.

After the anodic oxidation treatment, the surface of the aluminum may be treated as needed to render it hydrophilic. Examples of such hydrophilicization treatments which may be used in the present invention include the alkali metal silicate (such as sodium silicate aqueous solution) methods given in U.S. Pat. Nos. 2,714,066, 3,181,461, 3,280,734, and 3,902,734. In these methods, the support may be dipped in a sodium silicate aqueous solution or electrolytically treated. The methods of treatment with potassium fluorozirconate given in Japanese Examined Patent Application (Kokoku) 36-22063 or polyvinylphosphonic acid in U.S. Pat. Nos. 3,276,868, 4,153,461, or 4,689,272 may also be used.

An undercoat layer can be provided as needed between the support and the photosensitive layer. Various organic compounds may be used as components in the undercoat layer, such as carboxymethylcellulose, dextrin, gum arabic, 2-aminoethylphosphonic acid and similar amino group-containing phosphonic acids, optionally substituent-bearing phenylphosphonic acids, naphthylphosphonic acid, alkylphosphonic acids, griseophosphonic acid, methylenediphosphonic acid and ethylenediphosphonic acid or similar organic phosphonic acids, optionally substituent-bearing phenylphosphoric acid, naphthylphoshoric acid, alkylphosphoric acids and griseophosphoric acid or similar organic phosphoric acids, optionally substituent-bearing phenylphosphinic acid, naphthylphosphinic acid, alkylphosphinic acid and griseophosphonic acid or similar organic phosphinic acids, glycine or β-alanine and similar amino acids, and triethanolamine hydrochloride and similar hydroxy group-containing amine hydrochlorides. These may be used in combinations of two or more.

Organic undercoat layers can be provided in the following manner. The aforementioned organic compounds are dissolved in water or an organic solvent such as methanol, ethanol, or methyl ethyl ketone, or combinations thereof, and the resulting solution is applied on aluminum sheets and dried, or alternatively, the aforementioned organic compounds are dissolved in water or an organic solvent such as methanol, ethanol, or methyl ethyl ketone, or combinations thereof, the aluminum sheets are dipped in the resulting solution to allow the aforementioned compounds to adhere thereto, and the sheets are then washed with water or the like and dried, so as to provide an organic undercoat layer. Solution with a concentration of between 0.005 and 10 wt % of the aforementioned organic compounds can by applied by a variety of techniques in the aforementioned two methods. The solution concentration is between 0.01 and 20 wt %, and preferably between 0.05 and 5 wt %, in the latter method, the dipping temperature is between 20 and 90° C., and preferably between 25 and 50° C., while the dipping time is between 0.1 second and 20 minutes, and preferably between 2 seconds and 1 minute. The solution used therein can be prepared to a pH ranging between 1 and 12 with a basic substance such as ammonia, triethylamine, or potassium hydroxide, or an acidic substance such as hydrochloric acid or phosphoric acid. Yellow dyes can also be added to improve the tone reproducibility of the photosensitive composition.

The organic undercoat layer is applied in an amount of between 20 and 200 mg/m² and preferably between 5 and 100durability. The same is true with more than 200 mg/m².

The photosensitive composition that has been prepared is ordinarily exposed and developed to produce images. Examples of active light ray sources used during exposure include mercury lamps, metal halide lamps, xenon lamps, chemical lamps, and carbon arc lamps. Examples of radiation rays include electron beams, X-rays, ion beams, and far infrared rays. Other examples which can also be used include g rays, i rays, deep-UV light, and high density energy beams (laser beams). Examples of laser beams include helium-neon lasers, argon lasers, krypton lasers, helium-cadmium lasers, KrF excimer lasers, solid state lasers, and semiconductor lasers. In the present invention, light sources with an emission wavelength from the near infrared to infrared regions are preferred. Solid state lasers and semiconductor lasers are particularly preferred.

Conventionally known alkaline aqueous solutions can be used as the developer and replenisher. Examples include sodium silicate, potassium silicate, tribasic sodium phosphate, tribasic potassium phosphate, tribasic ammonium phosphate, dibasic sodium phosphate, dibasic potassium phosphate, dibasic ammonium phosphate, sodium carbonate, potassium carbonate, ammonium carbonate, sodium bicarbonate, potassium bicarbonate, ammonium bicarbonate, sodium borate, potassium borate, ammonium borate, sodium hydroxide, ammonium hydroxide, potassium hydroxide, lithium hydroxide and similar inorganic alkali salts. Other examples include monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine, pyridine and similar organic alkali agents.

Such alkali agents can be used alone or in combinations of two or more.

Particularly desirable developers among such alkali agents include aqueous solution of silicates such as sodium silicate and potassium silicate because they allow the development properties to be adjusted depending on the concentration and the ratio between the alkali metal oxide $M_2O$ (M represents an alkali metal) and the silicon oxide $SiO_2$ serving as a component in the silicate. Alkali metal silicates such as those given in Japanese Patent Application Laid-Open (JP-A) Nos.54-62004 and 57-7427 are effective.

When automatic developing machines are used, it is known that greater amounts of a photosensitive composition can be used without replacing the developer in the development tank for longer periods of time by adding an aqueous solution (replenisher) with higher alkaline strength than the developer to the developer. The use of this method of replenishment is preferred in the present invention as well. Various surfactants and organic solvents can be added to the developer and replenisher as needed to promote or inhibit development, and to improve the dispersion of the development gas and the ink affinity of the photosensitive composition for the areas without any images. Desirable surfactants include anionic, cationic, nonionic, and amphoteric surfactants. Hydroquinone, resorcin, sodium and potassium salts of inorganic acids such as sulfurous acid or hydrogensulfurous acid, and similar reducing agents, as well as organic carboxylic acids, defoaming agents, and hard water softeners can also be added as needed to the developer and replenisher.

The photosensitive composition which has been developed using the aforementioned developers and replenishers is post-treated with rinsing water, rinsing liquids containing surfactants and the like, or non-affinitizing liquids containing gum arabic or a starch derivative. Such treatments can be employed in various combinations as post-treatment when the photosensitive composition of the present invention is used for printing plates.

Automatic developing machines for printing plates are now being widely used to rationalize and standardize the manufacture of printing plates in the printing plate and printing industries. The photosensitive composition in the present invention can also be processed using automatic developing machines. Such automatic developing machines generally comprise a developer component and a post-treatment component, and comprise an apparatus for conveying the printing plates, various treatment solution tanks, and a spray apparatus wherein pumped processing solutions are sprayed through a spray nozzle as the exposed printing plates are horizontally conveyed during development. In a recent known method, the printing plates are processed by being dipped and transported by means of a guide roll or the like in the solution of processing tanks filled with processing solution. During such automatic processing, the process can be carried out as the processing solution is replenished with replenisher according to the amount of processing, operating time, and the like. So-called disposable processing can also be performed with essentially unused processing solution.

After image exposure, development, washing and/or rinsing and/or degumming, a device for removing the unneeded parts of an image can be used when there are unneeded image areas (such as film edge tracks of the source image film) on the photosensitive composition. A preferred example of such a removal method is the method in Japanese Examined Patent Application (Kokoku) 2-13293, where a removal solution is applied to the unneeded parts of the image, and is allowed to stand as such for a certain period of time, after which it is rinsed away. A method of development which is performed after active light rays from an optical fiber are directed onto the unneeded parts of the image, such as that in Japanese Patent Application Laid-Open (JP-A) No.59-174842, can also be used.

The photosensitive composition processed as described above can be coated with a non-affinitizing rubber as desired and then submitted to a printing process. A burning process may also be carried out to improve printing durability. When the photosensitive composition is subjected to a burning process, it should be treated with a conditioning solution such as that in Japanese Examined Patent Applications (Kokoku) 61-2518 and 55-28062 and Japanese Patent Application Laid-Open (JP-A) Nos.62-31859 and 61-159655. Examples of such methods include those in which the conditioning solution is applied with a sponge or absorbent cotton dipped in the conditioning solution onto the photosensitive composition, or the photosensitive composition is dipped in a vat filled with the conditioning solution, or the conditioning solution is applied with an automatic coater. Once applied, the amount of the solution should be evened out with a squeegee or a squeegee roller. The conditioning solution is generally applied in an amount of between 0.03 and 0.8 g/m$^2$ (dry weight).

After the photosensitive composition with the conditioning solution applied has been dried, it may be heated to an elevated temperature using a burning processor (such as the BP-1300 burning processor by Fuji Photo Film) or the like. The heating temperature and time depends on the type of components forming the image but should generally range between 180 and 300° C., and between 1 and 20 minutes.

The photosensitive composition having undergone such a burning process can then be treated as needed by conventional methods such as rinsing and degumming, but so-called non-affinitizing treatments such as degumming can be left out when a conditioning solution containing water-soluble polymer compounds or the like is used.

The photosensitive composition processed in this manner is incorporated in offset printing presses or the like for use in printing used paper or the like.

EXAMPLES

The present invention is described in detail below with reference to examples, but the present invention is not limited to these embodiments alone.

Synthesis Example 1

Synthesis of Compound A-1

Compound A-1 was synthesized in accordance with the following synthesis scheme.

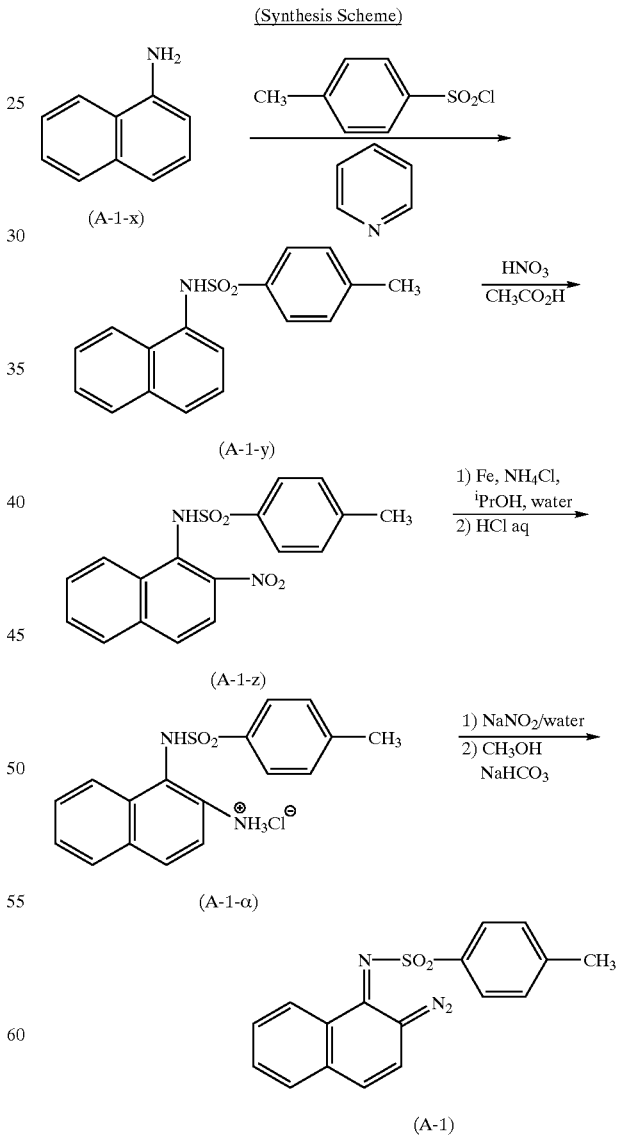

p-tosyl chloride (0.1 mol) and pyridine (100 mL) were introduced into a 500 mL pear-shaped flask, and α-naphthylamine A-1-x (0.1 mol) was added and stirred. Upon the addition of the α-naphthylamine A-1-x, the reaction mixture turned red, and heat was generated 30 minutes after it had been added. When the reaction mixture was cooled, crystals precipitated, and the reaction mixture turned orange. After the material had been stirred for 2 hours, 300 mL water was added to the reaction mixture, and HCl aq was added as the ingredients were stirred until the pH was less than 5, bringing about the precipitation of crystals. The precipitated crystals were filtered off, washed with HCl aq, and recrystallized using 500 mL methanol to give 23 g of A-1-y. The structure of the A-1-y was confirmed by NMR and the like.

The A-1-y (0.07 mol) and acetic acid (100 mL) were introduced into a 500 mL three-neck flask, and the addition of drops of 70% $HNO_3$ aq (0.07 mol) caused the reaction mixture to turn yellow. The mixture was allowed to stand for 1 day at room temperature, water (300 mL) and HCl (10 mL) were added, and the ingredients were stirred, resulting in the precipitation of crystals. The precipitated crystals were filtered off, and the resulting crude crystals were recrystallized from acetic acid and again from methanol, giving 1 g of A-1-z. The structure of the A-1-z was confirmed by NMR and the like.

Reduced Fe (0.012 mol), $NH_4Cl$ (0.001 mol), and water (0.5 mL) were introduced into a 100 mL three-neck flask and stirred at 90° C. A-1-z (0.002 mol) dissolved in isopropyl alcohol (30 mL) was added in the form of drops, the ingredients were stirred for 2 hours, and the reaction mixture was filtered using cerite. HCl aq (2 mL) was added to the resulting filtrate, and the material was concentrated in vacuo, giving 0.69 g of A-1-α in the form of a white powder. The structure of the A-1-α was confirmed by NMR and the like.

The A-1-α (0.002 mol) and methanol (30 mL) were introduced into a 100 mL beaker, and $NaNO_2$ (0.0025 mol) dissolved in water (3 mL) was added over an ice bath, resulting in red precipitate (pH was 4 at this time). The ingredients were stirred for 1 hour, and $NaHCO_3$ aq was added to adjust the pH to 8, resulting in yellow precipitate. The precipitate was filtered off and dried, giving 0.6 g of the target diazo compound A-1. The structure was confirmed by NMR and the like. The identification data for the diazo compound A-1 is given below. 1HNMR ($CDCl_3$, 300 MHz) δ 2.40 ppm (s, 3H, $CH_3$), 7.30 ppm (d, 2H, J=11.0 Hz, ArH (y)), 7.33 ppm (m, 1H, ArH (4)), 7.44 ppm (m, 1H, ArH (5)), 7.68 ppm (m, 3H, ArH (3), ArH (6), ArH (7)), 7.78 ppm (d, 2H, J=11.0 Hz, ArH (z)), 8.62 ppm (d, 1H, J=8.7 Hz, ArH (8)).

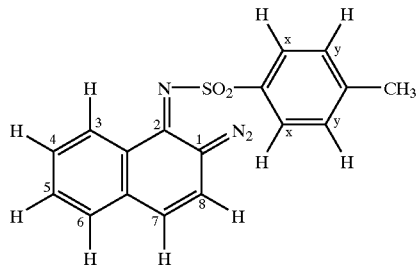

IR spectra (KBr radiation): ν (C=N'$^+$=N—)=2120 cm$^-$; UV spectra ($CHCl_3$ solution): λmax=421 nm; Melting point (dissolution point) 158° C.

The pKa of the dissociating H in the compound Ph—NH—Z was 12 to 13.

Synthesis Example 2

Synthesis of Compound A-10

Compound A-10 was synthesized in accordance with the following synthesis scheme.

(Synthesis Scheme)

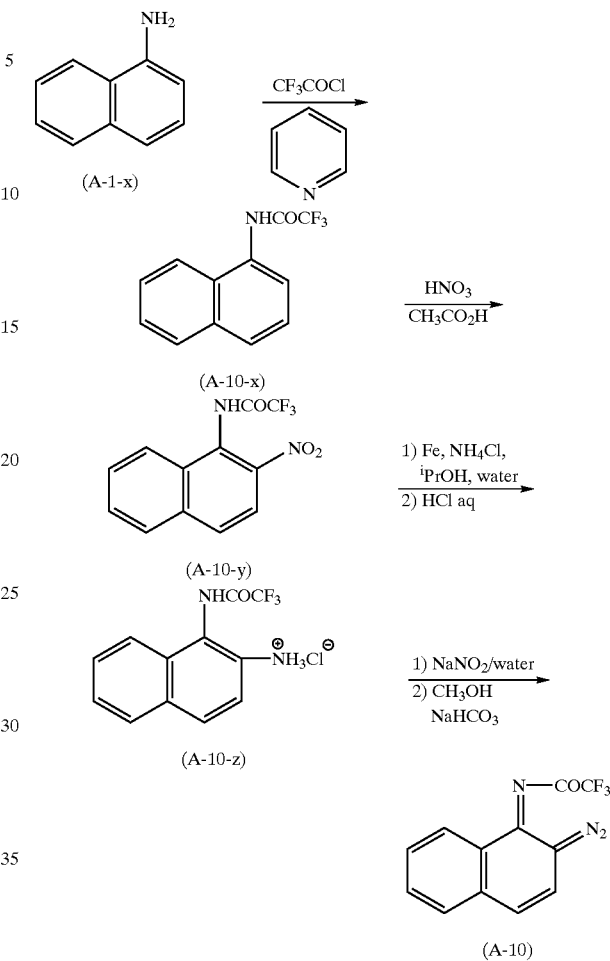

Trifluoroacetic chloride (0.1 mol) and pyridine (100 mL) were introduced into a 500 mL pear-shaped flask, and α-naphthylamine A-1-x (0.1 mol) was added and stirred. After the material had been stirred for 2 hours, 300 mL water was added to the reaction mixture, and HCl aq was added as the. ingredients were stirred until the pH was less than 5, bringing about the precipitation of crystals. The precipitated crystals were filtered off, washed with HCl aq, and recrystallized from methanol to give 17 g of A-10-x. The structure of the A-10-x was confirmed by NMR and the like.

The A-10-x (0.07 mol) and acetic acid (100 mL) were introduced into a 500 mL three-neck flask, and 70% $HNO_3$ aq (0.07 mol) was added in the form of drops. The reaction mixture was allowed to stand for 1 day at room temperature, water (300 mL) and HCl (10 mL) were added, and the ingredients were stirred, resulting in the precipitation of crystals. The precipitated crystals were filtered off, and the resulting crude crystals were isolated by silica gel column chromatography (ethyl acetate/hexane=25/75) and concentrated in vacuo, giving 5 g of A-10-y. The structure of the A-10-y was confirmed by NMR and the like.

Reduced Fe (0.04 mol); $NH_4Cl$ (0.004 mol), and water (2 mL) were introduced into a 300 mL three-neck flask and stirred at 90° C. A-10-y (0.008 mol) dissolved in isopropyl alcohol (100 mL) was added in the form of drops, the ingredients were stirred for 2 hours, and the reaction mixture was filtered using cerite. HCl aq (8 mL) was added to the resulting filtrate, and the material was concentrated in vacuo, giving 2.1 g of A-10-z in the form of a white powder. The structure of the A-10-z was confirmed by NMR and the like.

The A-10-z (0.002 mol) and methanol (30 mL) were introduced into a 100 mL beaker, and $NaNO_2$ (0.0025 mol) dissolved in water (3 mL) was added over an ice bath. The ingredients were stirred for 1 hour, and $NaHCO_3$ aq was added to adjust the pH to 9, resulting in yellow precipitate. The precipitate was filtered off and dried, giving 0.5 g of the target diazo compound A-10. The pKa of the dissociating H in the compound Ph—NH—Z was 13 to 14.

Synthesis Example 3

Synthesis of Compound B-1

Compound B-1 was synthesized in accordance with the following synthesis scheme.

(Synthesis Scheme)

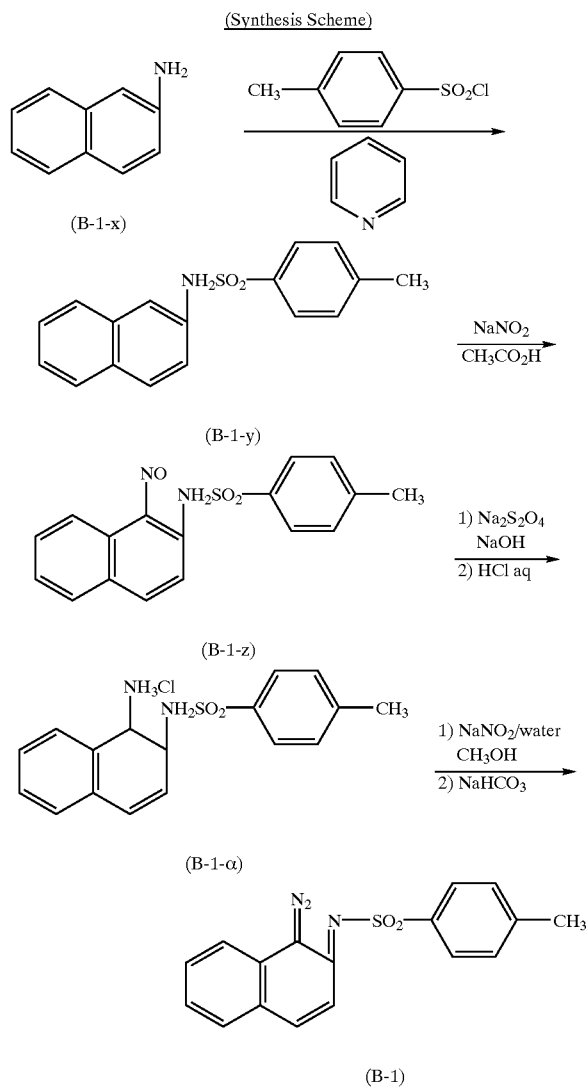

p-toluenesulfonyl chloride (0.1 mol) and pyridine (100 mL) were introduced into a 500 mL pear-shaped flask, and β-naphthylamine B-1-x (0.1 mol) was added and stirred. After the material had been stirred for 2 hours, 300 mL water was added to the reaction mixture, and HCl aq was added as the ingredients were stirred until the pH was less than 5, bringing about the precipitation of crystals. The precipitated crystals were filtered off, washed with HCl aq, and recrystallized from methanol to give 17 g of B-1-y. The structure of the B-1-y was confirmed by NMR and the like.

The B-1-y (0.05 mol) and acetic acid (100 mL) were introduced into a 500 mL three-neck flask, and $NaNO_2$ (0.06 mol) was added. The ingredients were stirred for 3 hours, and 300 mL of water was then added, resulting in the precipitation of crystals. The precipitated crystals were filtered off and recrystallized from methanol, giving 8 g of B-1-z. The structure of the B-1-z was confirmed by NMR and the like.

The B-1-z (0.02 mol), NaOH (0.04 mol), and water (200 mL) were introduced into a 500 mL beaker, and the ingredients were stirred. $Na_2S_2O_4$ (0.04 mol) was added to the reaction mixture, the ingredients were stirred for 3 hours, and the precipitated crystals were filtered off. The resulting crude crystals were washed with water and then dissolved in acetone, and HCl aq (3 mL) was added, resulting again in the precipitation of crystals. Ethyl acetate was added to bring about sufficient precipitation of crystals. The precipitated crystals were filtered off and washed with ethyl acetate, giving 6 g of B-1-α. The structure of the B-1-α was confirmed by NMR.

B-1-α (0.002 mol) and methanol (30 mL) were then introduced into a 100 mL beaker, and $NaNO_2$ (0.0025 mol) dissolved in water (3 mL) was added over an ice bath. The ingredients were stirred for 1 hour, and $NaHCO_3$ aq was added to adjust the pH to 8, resulting in yellow precipitate. The precipitate was filtered off and dried, giving 0.6 g of the target diazo compound B-1. The pKa of the dissociating H in the compound Ph—NH—Z was 12 to 13.

Synthesis Example 4

Synthesis of Compound C-3

Compound C-3 was synthesized in accordance with the following synthesis scheme.

(Synthesis Scheme)

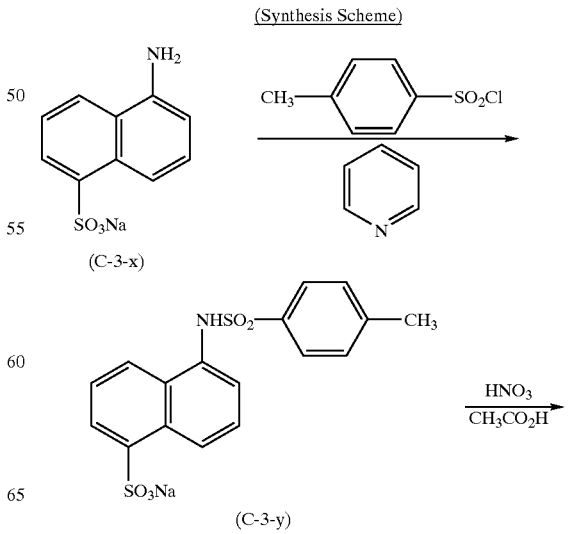

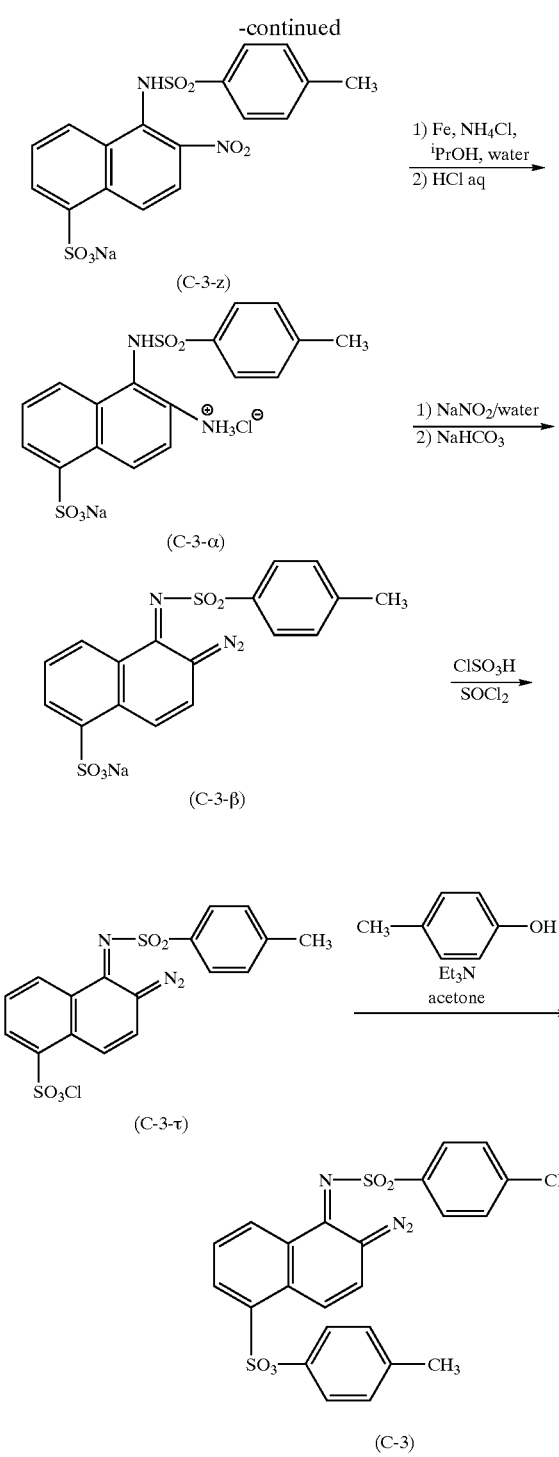

aq (0.05 mol) was added in the form of drops. The mixture was allowed to stand for 1 day, saturated aqueous NaCl (300 mL) was then added, and the ingredients were stirred, resulting in the precipitation of crystals. The resulting crude crystals were recrystallized again from saturated aqueous NaCl, giving 7 g of C-3-z. The structure of the C-3-z was confirmed by NMR and the like.

Reduced Fe (0.04 mol), NH$_4$Cl (0.004 mol), and isopropyl alcohol (100 mL) were introduced into a 300 mL three-neck flask and stirred at 90° C. C-3-z (0.008 mol) dissolved in water (10 mL) was added a little at a time. After the ingredients had been stirred for 2 hours, the reaction mixture was filtered using cerite. HCl aq (8 mL) was added to the resulting filtrate, and crystals were precipitated. The precipitated crystals were filtered off, giving 3.5 g of C-3-α. The structure of the C-3-α was confirmed by NMR and the like.

The C-3-α (0.004 mol) and water (30 mL) were then introduced into a 200 mL beaker, and NaNO$_2$ (0.005 mol) dissolved in water (6 mL) was added while cooled on ice. After the ingredients had been stirred for 1 hour, NaHCO$_3$ aq was added to adjust the pH to 9, resulting in yellow precipitate. The precipitate was filtered off and dried, giving 1.0 g of C-3-β. The structure of the C-3-β was confirmed by NMR and the like.

Chlorosulfonic acid (0.005 mol) and thionyl chloride (0.002 mol) were then introduced into a 200 mL pear-shaped flask, and the addition of C-3-β (0.002 mol) while cooled on ice resulted in an immediate reaction, with the solubilization of the reaction mixture. After the ingredients had been stirred for 1 hour, the reaction mixture was introduced into iced water, and the precipitated crystals were filtered off and dried, giving 0.7 g of C-3-γ The structure of the C-3-γ was confirmed by NMR.

C-3-γ (0.001 mol), acetone (30 mL), and p-cresol (0.001 mol)) were then introduced into a 100 mL beaker, and triethylamine (0.001 mol) was added while cooled on ice. The ingredients were stirred for 1 hour, and 50 mL water was added to the reaction mixture to precipitate crystals. The precipitated crystals were filtered off and dried, giving 0.4 g of the target diazo compound C-3.

Other diazo compounds represented by General Formula 1 given as examples in the Specification can by synthesized by methods similar to the above.

Diazo Compounds Used in Comparative Examples

The following diazo compounds were used in the comparative examples.

p-toluenesulfonyl chloride (0.1 mol) and pyridine (100 mL) were introduced into a 500 mL pear-shaped flask, and C-3-x (0.1 mol) was added and stirred. After the material had been allowed to stand for 1 day, 300 mL water was added to the reaction mixture, HCl aq was added as the ingredients were stirred until the pH was less than 5, and NaCl was added to bring about the precipitation of crystals. The precipitated crystals were filtered off and recrystallized from saturated aqueous NaCl to give 20 g of C-3-y. The structure of the C-3-y was confirmed by NMR and the like.

The C-3-y (0.05 mol) and acetic acid (100 mL) were introduced into a 500 mL three-neck flask, and 70% HNO$_3$

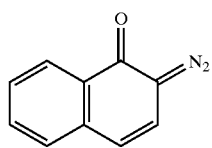 X-1
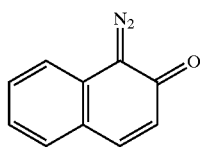 X-2
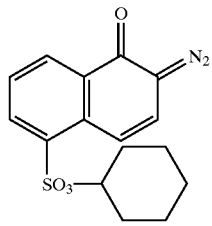 X-3
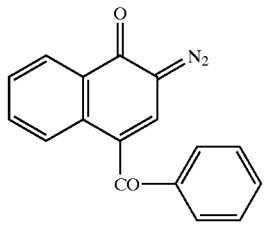 X-4
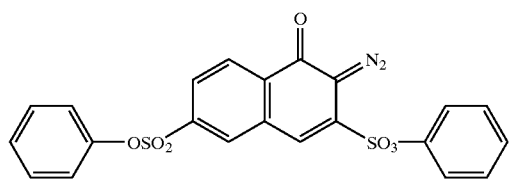 X-5
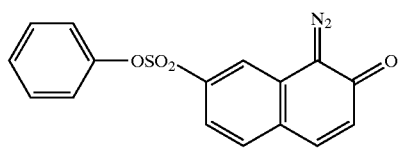 X-6
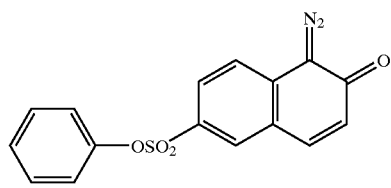 X-7
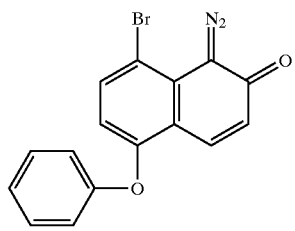 X-8
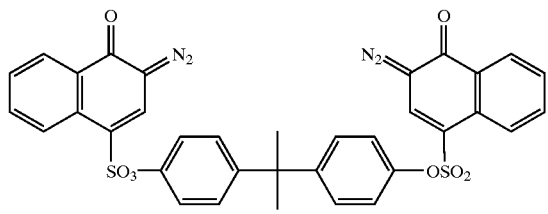 X-9
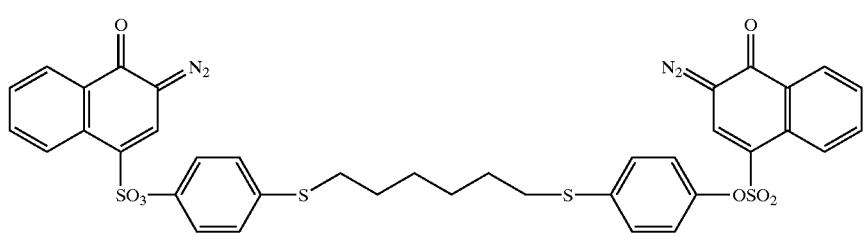 X-10

-continued
X-11
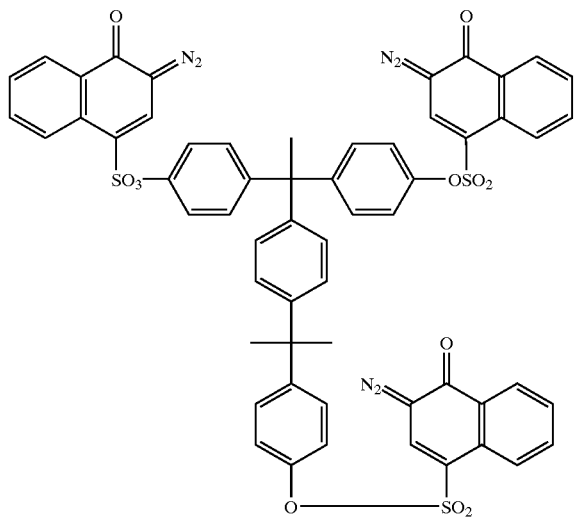
X-12
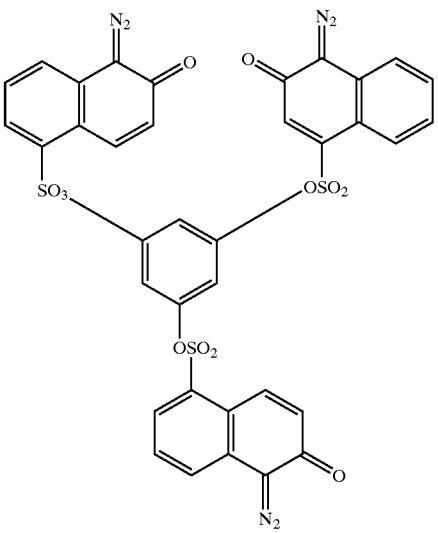
X-13
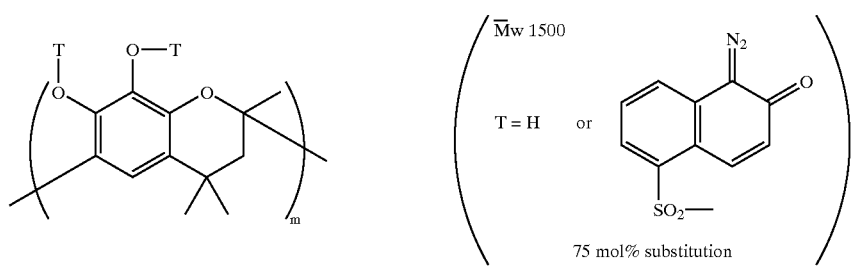
X-14
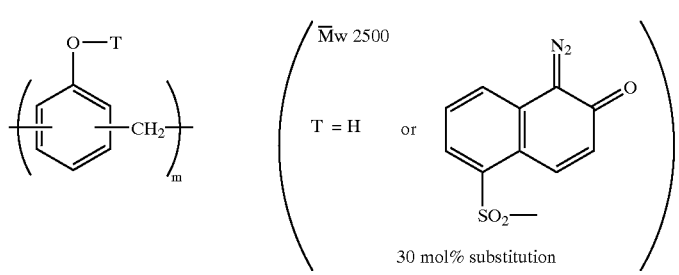
X-15
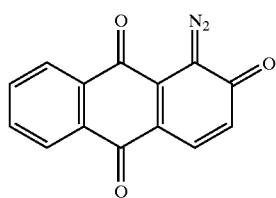
X-16
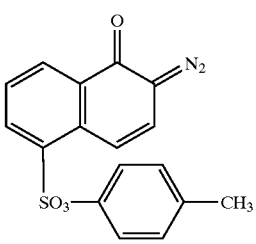
X-17
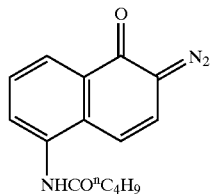
X-18
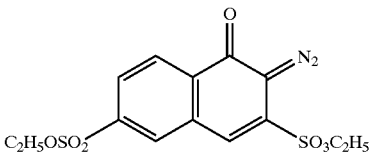

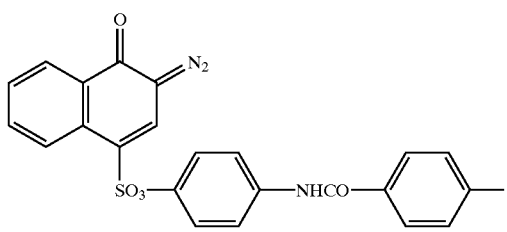

X-19

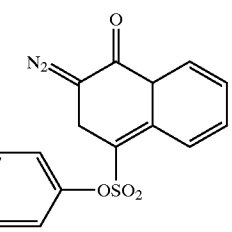

X-20

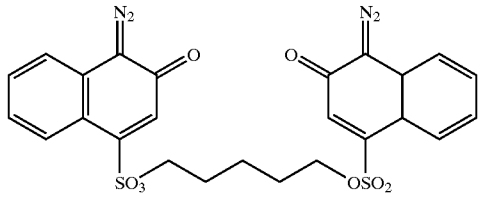

X-21

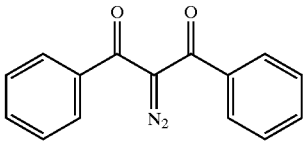

X-22

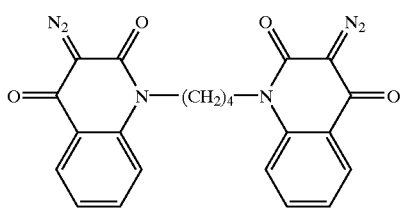

Synthesis of Water-Insoluble But Alkaline Water-Soluble Polymer

Synthesis of Copolymer P 31.0 g (0.36 mol) methacrylic acid, 39.1 g (0.36 mol) ethyl chloroformate, and 200 mL acetonitrile were introduced into a 500 mL three-neck flask with an agitator, condenser tube, and dropping funnel, and the resulting mixture was stirred while cooled in an iced water bath. 36.4 g (0.36 mol) triethylamine was added in the form of drops using the dropping funnel over about 1 hour to the mixture. When finished, the iced water bath was removed, and the mixture was stirred for 30 minutes at room temperature.

51.7 g (0.30 mol) p-aminobenzenesulfonamide was added to the reaction mixture, and the mixture was stirred for 1 hour while warmed to 70° C. in a hot water bath. Following the conclusion of the reaction, the resulting mixture was introduced into 1 L water as the water was stirred, and the resulting mixture was stirred for 30 minutes. The precipitate was filtered off from the mixture and was made into a slurry with the addition of 500 mL water, the slurry was filtered, and the solids that were obtained were dried, giving N-(p-aminosulfonylphenyl)methacrylamide in the form of a white solid (yield 46.9 g).

5.04 g (0.0210 mol) N-(p-amino sulfonylphenyl)methacrylamide, 2.05 g (0.0180 mol) ethyl methacrylate, 1.11 g (0.021 mol) acrylonitrile, and 20 g N,N-dimethyl acetamide were introduced into a 100 mL three-neck flask equipped with an agitator., condenser tube, and dropping funnel, and the mixture was stirred while warmed to 65° C. in a hot water bath. 0.15 g of 2,2'-azobis(2,4-dimethylvaleronitrile)(V-65, trademark by Wako Pure Chemicals) was added as a radical polymerization initiator to the mixture, and the mixture was stirred for 2 hours in a nitrogen stream while kept at 65° C. A mixture of 5.04 g N-(p-aminosulfonylphenyl)methacrylamide, 2.05 g ethyl methacrylate, 1.11 g acrylonitrile, 20 g N,N-dimethyl acetamide and 0.15 g of the aforementioned V-65 was added in the form of drops over 2 hours to the reaction mixture using the dropping funnel. When completed, the resulting mixture was stirred for another 2 hours at 65° C. Following the conclusion of the reaction, 40 g methanol was added to the mixture, which was cooled, the mixture was introduced into 2 L water as the water was stirred, the mixture was stirred for 30 minutes, and the precipitate was filtered off and dried, giving 15 g of copolymer P in the form of a white solid.

The weight-average molecular weight (based on polystyrene) of the copolymer P, as determined by gel permeation chromatography, was $5.3 \times 10^4$.

Examples 1 through 17, and Comparative Examples 1 through 15

(1) A photosensitive liquid 1 with the following composition was prepared.

Composition of Photosensitive Liquid 1

| | |
|---|---|
| Compound in Table 15 below | 0.25 g |
| IR absorbent (IR-1) | 0.20 g |
| m,p-cresol novolak (m/p ratio = 6/4, weight-average molecular weight 3500 unreacted cresol content 0.5 wt %) | 1.0 g |
| phenol novolak (weight-average molecular weight 7000) | 0.3 g |
| dye wherein the counterion of Victoria Pure Blue BOH is 1-naphthalenesulfonic acid anion | 0.02 g |
| fluorine surfactant (Megafac F-477, by Dainippon Ink and Chemicals) | 0.05 g |
| γ-butyrolactone | 3.0 g |
| methyl ethyl ketone | 8.0 g |
| 1-methoxy-2-propanol | 7.0 g |

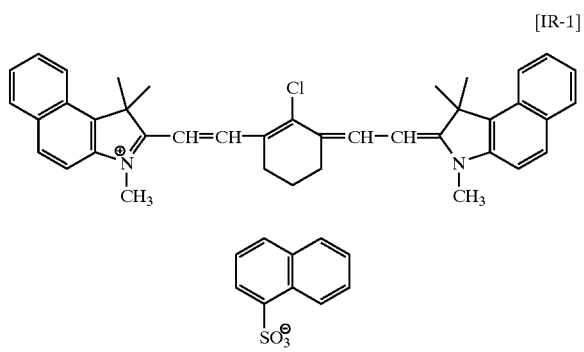

[IR-1]

TABLE 15

| No. | Compound of the invention used | No. | Corresponding comparative compound |
|---|---|---|---|
| Example 1 | A-1 | Comparative Example 1 | X-1 |
| Example 2 | A-10 | Comparative Example 1 | X-1 |
| Example 3 | B-2 | Comparative Example 2 | X-2 |
| Example 4 | B-22 | Comparative Example 2 | X-2 |
| Example 5 | C-6 | Comparative Example 3 | X-3 |
| Example 6 | C-14 | Comparative Example 4 | X-4 |
| Example 7 | C-18 | Comparative Example 5 | X-5 |
| Example 8 | D-1 | Comparative Example 6 | X-6 |
| Example 9 | D-2 | Comparative Example 7 | X-7 |
| Example 10 | D-21 | Comparative Example 8 | X-8 |
| Example 11 | E-2 | Comparative Example 9 | X-9 |
| Example 12 | E-7 | Comparative Example 10 | X-10 |
| Example 13 | E-16 | Comparative Example 11 | X-11 |
| Example 14 | F-14 | Comparative Example 12 | X-12 |
| Example 15 | F-19 (Mw 1500, 75 mol % substitution) | Comparative Example 13 | X-13 |
| Example 16 | F-20 (Mw 2500, 30 mol % substitution) | Comparative Example 14 | X-14 |
| Example 17 | G-2 | Comparative Example 15 | X-15 |

(2) Supports prepared by the following method were coated with the photosensitive liquid 1 such that the coated amount of the photosensitive liquid 1 to as 1.8 g/m², giving lithographic plates. These were used in Example s 1 through 17 and Comparative Examples 1 through 15.

Preparation of Support 0.3 mm thick aluminum sheets (material 1050) were degreased by being washed with trichloroethylene, the surface was then textured with a nylon brush and a 400 mesh pumice-water suspension, and the sheets were thoroughly washed with water. The aluminum sheets were etched by being dipped for 9 seconds in 25% sodium hydroxide aqueous solution at 45° C., and were then washed with water, dipped for another 20 seconds in 20% nitric acid, and washed with water. The textured surfaces were etched about 3 g/m² at this time. The aluminum sheets were then provided with 3 g/m² DC anodic oxidation films at a current density of 15 A/dm² using 7% sulfuric acid as the electrolyte, they were then washed with water and dried, the following undercoat liquid was applied, and the coated film was dried for 1 minute at 90° C. The dried coated film was 10 mg/M².

| Undercoat Liquid Composition | |
|---|---|
| β-alanine | 0.50 g |
| methanol | 95 g |
| water | 5.0 g |

Comparative Example 16

Comparative Example 16 was carried out by producing a lithographic plate in the same manner as in Example 1 except that no diazo compound was added during the preparation of the aforementioned photosensitive liquid 1.

Examples 18 through 27, and Comparative Examples 17 through 25

A photosensitive liquid 2 with the following composition was prepared.

Composition of photosensitive liquid 2

| | |
|---|---|
| Compound in Table 16 below | 0.25 g |
| IR absorbent (IR-2) | 0.20 g |
| copolymer P synthesized above | 0.5 g |
| m-cresol novolak | 0.5 g |
| (weight-average molecular weight 6000) | |
| phenol novolak | 0.1 g |
| (weight-average molecular weight 5000) | |
| dye wherein the counterion of Victoria | 0.02 g |
| Pure Blue BOH is 1-naphthalenesulfonic | |
| acid anion | |
| fluorine surfactant | 0.05 g |
| (Megafac F-177, by Dainippon Ink and Chemicals) | |
| γ-butyrolactone | 3.0 g |
| methyl ethyl ketone | 8.0 g |
| 1-methoxy-2-propanol | 7.0 g |

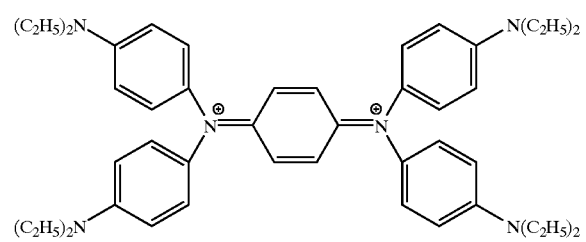

[IR-2]

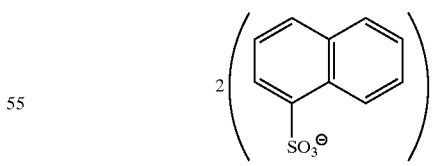

TABLE 16

| No. | Compound of the invention used | No. | Corresponding comparative compound |
|---|---|---|---|
| Example 18 | A-3 | Comparative Example 17 | X-1 |

TABLE 16-continued

| No. | Compound of the invention used | No. | Corresponding comparative compound |
|---|---|---|---|
| Example 19 | A-13 | Comparative Example 17 | X-1 |
| Example 20 | B-16 | Comparative Example 18 | X-2 |
| Example 21 | C-3 | Comparative Example 19 | X-16 |
| Example 22 | C-20 | Comparative Example 20 | X-17 |
| Example 23 | D-19 | Comparative Example 21 | x-18 |
| Example 24 | E-12 | Comparative Example 22 | X-19 |
| Example 25 | F-13 | Comparative Example 23 | X-20 |
| Example 26 | G-3 | Comparative Example 24 | X-21 |
| Example 27 | G-21 | Comparative Example 25 | X-22 |

Supports prepared in the same manner as above were coated with the photosensitive liquid 2 such that the coated amount of the photosensitive liquid 1 to as 1.8 g/m$^2$, giving lithographic plates. These were used in Examples 18 through 27 and Comparative Examples 17 through 25.

Comparative Example 26

Comparative Example 26 was obtained by producing a lithographic plate in the same manner as in Example 18 except that no diazo compound was added during the preparation of the aforementioned photosensitive liquid 2.

The performance of the lithographic plates obtained in Examples 1 through 27 and Comparative Examples 1 through 26 prepared above was evaluated based on the following criteria.

Evaluation of Sensitivity and Development Latitude

The lithographic plates of the Examples and Comparative Examples were exposed using a semiconductor laser with a wavelength of 840 nm or a YAG laser with a wavelength of 1064 nm. The laser used was selected according to the absorption wavelength of the IR absorbent that was contained. The exposed plates were developed using an automatic developing machine (PS Processor 900 VR, by Fuji Photo film) filled with Developer DP-4 and Rinse Solution FR-3 (1:7) by Fuji Photo Film. The Developer DP-4 was prepared in two levels, one diluted to a ratio of 1:6, the other to a ratio of 1:12.

The line width of the areas with no images obtained using the DP-4 developer diluted to 1:6 was measured, and the laser radiation energy corresponding to that line width was determined as an index of sensitivity (mJ/cm$^2$). The lower the measured value (mJ/cm$^2$), the higher the lithographic plate sensitivity.

The line widths of areas with no images obtained using the developer diluted to 1:6 and developer diluted to 1:12 were then measured, the laser radiation energy corresponding to those line widths was determined, and the difference between the sensitivity of the two was used as an index of development latitude. The lower the difference, the better the development latitude. A level of no more than 20 mJ/cM$^2$ was useable for practical purposes.

Evaluation of Storage Stability

The lithographic plates of the examples were stored for 3 days at a temperature of 60° C. and a humidity of 45% RH. This was followed by laser exposure and development in the same manner as above, and the sensitivity was similarly determined and compared with the previous results to determine the difference as an index of storage stability. A change in sensitivity of no more than 20 mJ/cm$^2$ indicated favorable storage stability and was useable for practical purposes.

The results are given in Tables 17 and 18 below.

TABLE 17

| No. | Exposure wavelength (nm) | Sensitivity (mJ/cm$^2$) | Development latitude (mJ/cm$^2$) | Storage stability (mJ/cm$^2$) |
|---|---|---|---|---|
| Example 1 | 840 | 110 | 10 | 10 |
| Example 2 | 840 | 110 | 15 | 10 |
| Example 3 | 840 | 110 | 10 | 10 |
| Example 4 | 840 | 110 | 10 | 10 |
| Example 5 | 840 | 120 | 10 | 15 |
| Example 6 | 840 | 120 | 10 | 10 |
| Example 7 | 840 | 120 | 5 | 10 |
| Example 8 | 840 | 120 | 10 | 10 |
| Example 9 | 840 | 115 | 10 | 10 |
| Example 10 | 840 | 110 | 10 | 5 |
| Example 11 | 840 | 120 | 10 | 10 |
| Example 12 | 840 | 115 | 15 | 10 |
| Example 13 | 840 | 110 | 10 | 10 |
| Example 14 | 840 | 115 | 10 | 10 |
| Example 15 | 840 | 110 | 10 | 10 |
| Example 16 | 840 | 115 | 15 | 15 |
| Example 17 | 840 | 120 | 10 | 10 |
| Comp. Ex. 1 | 840 | 130 | 40 | 40 |
| Comp. Ex. 2 | 840 | 135 | 30 | 40 |
| Comp. Ex. 3 | 840 | 140 | 30 | 40 |
| Comp. Ex. 4 | 840 | 130 | 30 | 40 |
| Comp. Ex. 5 | 840 | 130 | 30 | 40 |
| Comp. Ex. 6 | 840 | 140 | 40 | 40 |
| Comp. Ex. 7 | 840 | 150 | 40 | 50 |
| Comp. Ex. 8 | 840 | 140 | 30 | 40 |
| Comp. Ex. 9 | 840 | 140 | 30 | 40 |
| Comp. Ex. 10 | 840 | 150 | 40 | 35 |
| Comp. Ex. 11 | 840 | 150 | 30 | 30 |
| Comp. Ex. 12 | 840 | 145 | 30 | 30 |
| Comp. Ex. 13 | 840 | 150 | 30 | 30 |
| Comp. Ex. 14 | 840 | 140 | 30 | 30 |
| Comp. Ex. 15 | 840 | 150 | 40 | 40 |
| Comp. Ex. 16 | 840 | 130 | 40 | 40 |

TABLE 18

| No. | Exposure wavelength (nm) | Sensitivity (mJ/cm$^2$) | Development latitude (mJ/cm$^2$) | Storage stability (mJ/cm$^2$) |
|---|---|---|---|---|
| Example 18 | 1064 | 110 | 10 | 10 |
| Example 19 | 1064 | 120 | 10 | 10 |
| Example 20 | 1064 | 120 | 15 | 15 |
| Example 21 | 1064 | 110 | 10 | 10 |
| Example 22 | 1064 | 110 | 10 | 10 |
| Example 23 | 1064 | 115 | 10 | 5 |
| Example 24 | 1064 | 110 | 5 | 10 |
| Example 25 | 1064 | 110 | 10 | 10 |
| Example 26 | 1064 | 120 | 10 | 10 |
| Example 27 | 1064 | 110 | 10 | 10 |
| Comp. Ex. 17 | 1064 | 130 | 40 | 30 |
| Comp. Ex. 18 | 1064 | 135 | 40 | 30 |
| Comp. Ex. 19 | 1064 | 140 | 40 | 30 |
| Comp. Ex. 20 | 1064 | 140 | 30 | 30 |
| Comp. Ex. 21 | 1064 | 140 | 30 | 40 |
| Comp. Ex. 22 | 1064 | 135 | 30 | 40 |
| Comp. Ex. 23 | 1064 | 135 | 40 | 40 |
| Comp. Ex. 24 | 1064 | 130 | 40 | 40 |
| Comp. Ex. 25 | 1064 | 135 | 40 | 40 |
| Comp. Ex. 26 | 1064 | 130 | 50 | 40 |

The above results show that the lithographic plates in Examples 1 through 27 had higher sensitivity for IR lasers than did the lithographic plates in Comparative Examples 1 through 26, and that there was far less difference in sensitivity when the aforementioned developers with two levels were used, indicating sufficient development latitude for practical purposes. The lithographic plates of Examples 1 through 27 also all had far lower fluctuations in sensitivity before and after storage compared to the lithographic plates of Comparative Examples 1 through 26, indicating better storage stability at a level satisfactory for practical use.

Examples 28 through 32, and Comparative Examples 27 through 32

A photosensitive liquid 3 with the following composition was prepared.
Composition of photosensitive liquid 3

| Compound in Table 19 below | 0.3 g |
| --- | --- |
| m,p-cresol novolak (m/p ratio = 7/3, weight-average molecular weight 5000) | 1.0 g |
| poly-p-hydroxystyrene (weight-average molecular weight 20,000) | 0.2 g |
| dye wherein the counterion of Victoria Pure Blue BOH is 1-naphthalenesulfonic acid anion | 0.02 g |
| fluorine surfactant (Megafac F-177, by Dainippon Ink and Chemicals) | 0.05 g |
| methanol | 3.0 g |
| methyl ethyl ketone | 8.0 g |
| 1-methoxy-2-propanol | 7.0 g |

TABLE 19

| No. | Invention compound or comparative compound |
| --- | --- |
| Example 28 | A-1 |
| Example 29 | D-2 |
| Example 30 | E-2 |
| Example 31 | F-20 ($\overline{Mw}$ 2500, 30 mol % substitution) |
| Example 32 | G-21 |
| Comparative Example 27 | X-1 |
| Comparative Example 28 | X-7 |
| Comparative Example 29 | X-9 |
| Comparative Example 30 | X-14 |
| Comparative Example 31 | X-22 |
| Comparative Example 32 | No compound added |

Supports prepared in the same manner as in Example 1 were coated with the photosensitive liquid 3 such that the coated amount of the photosensitive liquid 1 to as 1.8 g/m$^2$, giving the lithographic plates used in Examples 28 through 32 and Comparative Examples 27 through 32.

The performance of the lithographic plates obtained in Examples 28 through 32 and Comparative Examples 27 through 32 prepared above was evaluated based on the following criteria. The results are given in Table 20
Evaluation of Sensitivity and Dry Durability A gray scale with a density difference of 0.15 was attached to the photosensitive layer of the lithographic plates, which were exposed for 2 minutes using a 2 kw high pressure mercury lamp at a distance of 50 cm. The exposed printing plates were developed for 30 seconds at 25° C. in DP-4 diluted with water to 1:8. The number of clear steps in the resulting gray scale at this time was read as an index of sensitivity. A greater number of steps indicates higher sensitivity.

Unexposed printing plates were dried in vacuo for 24 hours at 60° C., and were exposed using a mercury lamp in the same manner as above and developed. The number of clear steps in the resulting gray scale at this time was read, and the difference in the number of clear steps of the aforementioned undried plates was used as an index of dry durability. A difference of 1 or less steps is preferred for practical purposes.

TABLE 20

| No. | Sensitivity (number of clear steps) | Dry durability (difference in number of clear steps) |
| --- | --- | --- |
| Example 28 | 7 | 0.75 |
| Example 29 | 7 | 1.0 |
| Example 30 | 8 | 0.75 |
| Example 31 | 8 | 1.0 |
| Example 32 | 7 | 0.75 |
| Comparative Example 27 | 6 | 3 |
| Comparative Example 28 | 6 | 4 |
| Comparative Example 29 | 5 | 4 |
| Comparative Example 30 | 5 | 3 |
| Comparative Example 31 | 5 | 4 |
| Comparative Example 32 | no images | — |

The results in Table 20 show that the lithographic plates of the examples retained particularly high sensitivity when dry, that is, better printability with heat modes involving low moisture.

In view of the foregoing, the positive photosensitive composition of the present invention is highly sensitive to heat mode lasers, and has better development latitude and better storage stability.

Further, the novel diazo compound of the present invention represented by general formula (I) is useful as a material for positive lithographic printing plates, and in particular, as a material for lithographic printing plates for heat mode recording, and in addition, can be used as an agent which efficiently generates an acid upon application of light and/or heat, which agent has a wide range of uses for various types of image forming materials. For example, the diazo compound of the present invention can be used in (1) a color image forming material formed by a combination of the diazo compound and a dye which is acidic and generates color or eliminates color, or (2) a negative image forming material formed by a combination of the diazo compound and a binder which cross-links due to an acid catalyst, or the like. The distinguishing features of the diazo compound used for such applications are that a strong acid can be effectively generated, and the image forming materials formed from the diazo compound have good storage stability.

Hereinafter, the (1) color image forming material will be explained in detail by Examples 33 through 36 and Comparative Examples 33 through 35, and the (2) negative image forming material will be described in detail by Examples 37 through 40 and Comparative Examples 36 through 38. However, it is to be understood that the present invention is not to be limited to these Examples.

Examples Relating to (1) Color Image Forming Material (Substrate)
After an aluminum plate (substance 1050) of a thickness of 0.30 mm was subjected to a degreasing treatment, the surface thereof was roughened by using a nylon brush and a 400-mesh pumice stone/water suspension. The aluminum plate was then washed well with water. Next, the aluminum plate was immersed for 9 seconds in a 25% sodium oxide aqueous solution of 45° C. so that etching was carried out. The aluminum plate was then washed with water, and thereafter was immersed for 20 seconds in 2% HNO$_3$ and was washed. The amount of etching of the roughened surface was about 3 g/m$^2$. Next, a direct current anodic oxidized film of 3 g/m$^2$ was formed by subjecting the plate to electrolysis at a current density of 15A/dm² by using 7% H₂SO₄ as the electrolyte. Thereafter, the plate was rinsed and dried. Next, the following coating solution was applied onto the aluminum plate, and the plate was dried at 80° C. for 30 seconds so as to obtain a substrate. The amount of the coated film after drying was 10 mg/m².

Examples 33 through 36

The following color image forming material solution, which contained a compound of the present invention as shown in Table 21, was coated on the aforementioned substrate, and the coated substrate was dried for 1 minute at 100° C. The weight after drying was 1.5 g/m².

Comparative Examples 33 through 35

Coated substrates were prepared in the same manner as in Examples 33 through 36 except that a general, well-known acid generating agent was used as the acid generating agent.

(Color Image Forming Material Solution)

| | |
|---|---|
| methyl polymethacrylate (weight average molecular weight 50,000) | 1.5 g |
| N-octylindole | 0.3 g |
| phthalaldehyde | 0.3 g |
| compound of the present invention (as listed in Table 21) | 0.3 g |
| methylethylketone | 15.0 g |
| acetone | 4.0 g |

(Evaluation of Sensitivity)

The photosensitive material was scan-exposed by a laser having a light emitting range of 250 nm to 400 nm, and was then left to stand for one hour. The red coloration was measured by using a Macbeth densitometer, and the relative sensitivity was determined. The higher the value, the better the sensitivity.

(Evaluation of Storage Stability)

The photosensitive material which had not yet been exposed by laser was left to stand for three days in high humidity (75% RH, 45° C.), and a Macbeth densitometer was used to determine whether there was any color fogging.

The results of these evaluations are listed in Table 21.

TABLE 21

Results of Evaluations

| | Compound of the Present invention | Relative Sensitivity | Storage Stability |
|---|---|---|---|
| Example 33 | A-2 | 100 | good |
| Example 34 | A-11 | 110 | good |
| Example 35 | B-5 | 100 | good |
| Example 36 | C-13 | 100 | good |
| Comp. Ex. 33 | V-1 | 80 | fogging |
| Comp. Ex. 34 | V-2 | 70 | fogging |
| Comp. Ex. 35 | V-3 | 10 | good |

Compounds in Table 21:

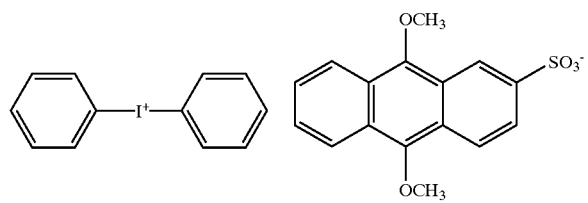

V-1

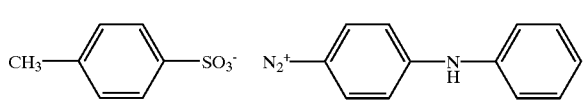

V-2

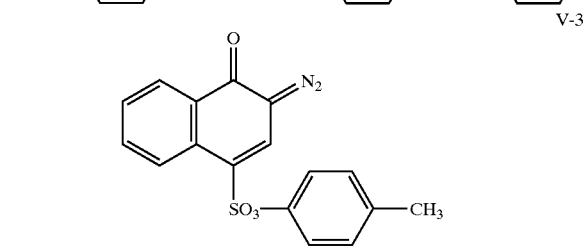

V-3

From the results of Table 21, it can be seen that the photosensitive materials using the compounds of the present invention had high sensitivity and good storage stability.

Examples Relating to (2) Negative Image Forming Material

Examples 37–40

The following negative image forming material solution, which contained a compound of the present invention as shown in Table 22, was coated on the aforementioned substrate, and the coated substrate was dried for 1 minute at 100° C. The weight after drying was 1.3 g/m².

Comparative Examples 36 through 38

Coated substrates were prepared in the same manner as in Examples 37 through 40 except that a general, well-known acid generating agent was used as the acid generating agent.

(Negative Image Forming Material Solution)

| | |
|---|---|
| poly-p-hydroxystyrene (weight average molecular weight 50000) | 1.5 g |
| p-divinylbenzene | 0.8 g |
| tetrabutylammonium acetate | 0.03 g |
| compound of the present invention (as listed in Table 22) | 0.3 g |
| methylethylketone | 15.0 g |
| methanol | 4.0 g |

(Evaluation of Sensitivity)

The photosensitive/heat-sensitive material was scan-exposed by a laser having a light emitting range of 250 nm to 400 nm. After exposure, the material was subjected to heating processing for 60 seconds at 130° C. by using a panel heater. Thereafter, the material was developed by using developer DP-4 (a 1:8 water-diluted solution) manufactured by Fuji Photo Film Co., Ltd. The amount of energy required for recording was computed on the basis of the line width of the image obtained at this time, the laser output, the loss of the optical system, and the scanning speed. The relative sensitivity was determined, and the higher the value, the higher the sensitivity.
(Evaluation of Storage Stability)

The photosensitive material which had not yet been exposed by laser was left to stand for three days in high humidity (75% RH, 45° C.). Thereafter, the material was printed, and staining in the non-image portions was evaluated. Stains appeared in the non-image portions of those materials having poor storage stability.

The results of these evaluations are listed in Table 22.

TABLE 22

| | Results of Evaluations | | |
|---|---|---|---|
| | Compound of the Present Invention | Relative Sensitivity | Storage Stability |
| Example 37 | A-5 | 100 | good |
| Example 38 | B-2 | 100 | good |
| Example 39 | E-4 | 120 | good |
| Example 40 | F-17 | 120 | good |
| Comp. Ex. 36 | V-1 | 80 | stains present |
| Comp. Ex. 37 | V-2 | 70 | stains present |
| Comp. Ex. 38 | V-3 | did not cure | good |

From the results of Table 22, it can be seen that the photosensitive materials using the compounds of the present invention had high sensitivity and good storage stability.

What is claimed is:

1. A positive photosensitive composition, comprising at least a diazo compound represented by the following General Formula 1, and a water-insoluble but alkaline water-soluble polymer:

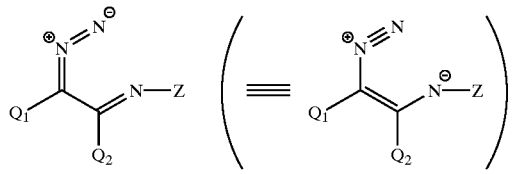

(1)

wherein z represents an organic group in which the pKa of dissociating H in Ph—NH—Z is no more than 14, and $Q^1$ and $Q^2$ represent organic groups, where $Q^1$ and $Q^2$ may be bonded to form an aliphatic ring or aromatic ring and wherein when Z is —$SO_2R^1$, $R^1$ is a terminal group.

2. A positive photosensitive composition according to claim 1, wherein $R^2$ is a hydrocarbon group having an electron-attracting substituent selected from the group consisting of halogen atoms, substituted sulfonyl groups, nitro groups, cyano groups, alkoxy groups, and hydroxy groups.

3. A positive photosensitive composition according to claim 1, wherein the hydrocarbon group $R^1$ is a hydrocarbon group selected from the group consisting of alkyl groups, substituted alkyl groups, aryl groups, substituted aryl groups, alkenyl groups, substituted alkenyl groups, alkinyl groups, and substituted alkinyl groups.

4. A positive photosensitive composition according to claim 1, wherein the organic groups $Q^1$ and $Q^2$ are selected from the group consisting of hydrocarbon groups, heterocyclic groups, substituted oxy groups, substituted thio groups, substituted amino groups, substituted carbonyl groups, substituted sulfinyl groups, substituted sulfonyl groups, substituted phosphono groups, substituted phosphonato groups, substituted phosphoryl groups, and cyano groups.

5. A positive photosensitive composition according to claim 1, wherein the diazo compound is an acid-producing agent that produces acid by being decomposed upon exposure to light.

6. A positive photosensitive composition according to claim 5, wherein the diazo compound, when decomposed upon exposure to light, is capable of producing acid without the alkaline water-insoluble polymer becoming insoluble in alkaline water.

7. A positive photosensitive composition according to claim 1, further comprising an infrared absorbent.

8. A positive photosensitive composition that is sensitive to a heat mode laser, comprising at least a diazo compound represented by General Formula 1, and a water-insoluble but alkaline water-soluble polymer:

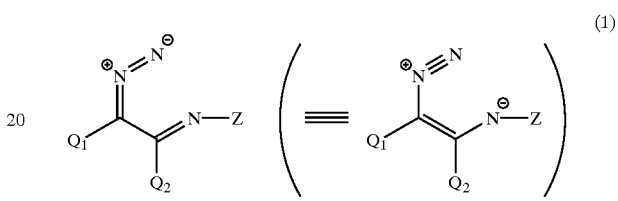

(1)

wherein z represents an organic group in which the pKa of dissociating H in Ph—NH—Z is no more than 14, and $Q^1$ and $Q^2$ represent organic groups, where $Q^1$ and $Q^2$ may be bonded to form an aliphatic ring or aromatic ring and wherein when Z is —$SO_2R^1$, $R^1$ is a terminal group.

9. A positive photosensitive composition according to claim 8, wherein the organic group Z in General Formula 1 represents —$SO_2R^1$ or —$COR^2$ wherein $R^1$ represents a hydrocarbon group, and $R^2$ represents a hydrocarbon group with an electron-attracting substituent.

10. A positive photosensitive composition according to claim 9, wherein the hydrocarbon group $R^2$ has an electron-attracting substituent selected from the group consisting of halogen atoms, substituted sulfonyl groups, nitro groups, cyano groups, alkoxy groups, and hydroxy groups.

11. A positive photosensitive composition according to claim 9, wherein the hydrocarbon group $R^1$ in General Formula 1 is selected from the group consisting of alkyl groups, substituted alkyl groups, aryl groups, substituted aryl groups, alkenyl groups, substituted alkenyl groups, alkinyl groups, and substituted alkinyl groups.

12. A positive photosensitive composition according to claim 9, wherein the organic groups $Q^1$ and $Q^2$ are selected from the group consisting of hydrocarbon groups, heterocyclic groups, substituted oxy groups, substituted thio groups, substituted amino groups, substituted carbonyl groups, substituted sulfinyl groups, substituted sulfonyl groups, substituted phosphono groups, substituted phosphonato groups, substituted phosphoryl groups, and cyano groups.

13. A positive photosensitive composition according to claim 8, wherein the diazo compound is an acid-producing agent that produces acid by being decomposed upon exposure to light.

14. A positive photosensitive composition according to claim 13, wherein the diazo compound, when decomposed upon exposure to light, is capable of producing acid without the alkaline water-insoluble polymer becoming insoluble in alkaline water.

15. A positive photosensitive composition according to claim 8, further comprising an infrared absorbent.

16. A diazo compound represented by the following general Formula 1:

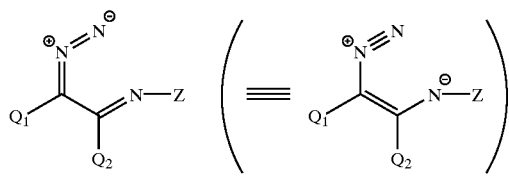 (1)

wherein Z represents an organic group in which the pKa of dissociating H in Ph—NH—Z is no more than 14, and $Q^1$ and $Q^2$ represent organic groups, where $Q^1$ and $Q^2$ are bonded to form an aromatic ring and wherein when Z is —$SO_2R^1$, $R^1$ is a terminal group.

17. A diazo compound according to claim 16, wherein the organic group Z in General Formula 1 represents —$SO_2R^1$ or —$COR^2$, wherein $R_1$ represents a hydrocarbon group, and $R^2$ represents a hydrocarbon group with an electron-attracting substituent.

18. A diazo compound according to claim 17, wherein the hydrocarbon group $R^2$ in General Formula 1 has an electron-attractive substituent selected from the group consisting of halogen atoms, substituted sulfonyl groups, nitro groups, cyano groups, alkoxy groups, and hydroxy groups.

19. A positive photosensitive composition according to claim 1, wherein Z is —$COR^2$ wherein $R^2$ represents a hydrocarbon group with an electron-attracting substitutent.

20. A positive photosensitive composition according to claim 8, wherein Z is —$COR^2$ wherein $R^2$ represents a hydrocarbon group with an electron-attracting substitutent.

21. A diazo compound according to claim 16, wherein Z is —$COR^2$ wherein $R^2$ represents a hydrocarbon group with an electron-attracting substitutent.

22. A positive photosensitive composition according to claim 1, wherein $Q^1$ and $Q^2$ are bonded to form an aromatic ring.

23. A positive photosensitive composition according to claim 8, wherein $Q^1$ and $Q^2$ are bonded to form an aromatic ring.

* * * * *